United States Patent [19]
Amara et al.

[11] Patent Number: 5,989,825
[45] Date of Patent: Nov. 23, 1999

[54] EXCITATORY AMINO ACID TRANSPORTER GENE AND USES

[75] Inventors: Susan G. Amara, Portland, Oreg.; Jeffrey L. Arriza, Kennett Square, Pa.; Scott Eliasof; Michael P. Kavanaugh, both of Portland, Oreg.

[73] Assignee: Oregon Health Sciences University, Portland, Oreg.

[21] Appl. No.: 09/188,469

[22] Filed: Nov. 9, 1998

Related U.S. Application Data

[60] Division of application No. 08/948,569, Oct. 10, 1997, Pat. No. 5,882,926, which is a continuation-in-part of application No. 08/140,729, Oct. 20, 1993, Pat. No. 5,658,782
[60] Provisional application No. 60/028,325, Oct. 11, 1996.

[51] Int. Cl.$^6$ ............. C12Q 1/68; G01N 33/53; G01N 33/566; C12P 21/04
[52] U.S. Cl. ............. 435/6; 435/7.8; 435/20; 435/69.1; 435/70.1; 436/501; 436/504
[58] Field of Search ............. 435/6, 7.8, 29, 435/69.1, 70.1; 436/501, 504

[56] References Cited

U.S. PATENT DOCUMENTS

| | | | |
|---|---|---|---|
| 4,683,195 | 7/1987 | Mullis | 435/6 |
| 5,385,831 | 1/1995 | Mulvihill et al. | 435/69.1 |
| 5,424,185 | 6/1995 | Lam et al. | 435/6 |
| B1 4,683,202 | 11/1990 | Mullis | 435/91 |

OTHER PUBLICATIONS

Arriza et al. (1994) J. Neurosci., vol. 14, No. 9, pp. 5559–5569.
Kanai et al. (1992) Nature, 360: 467–471.
Kanai et al. (1993) Trends in Neurosci., vol. 16, No. 9, pp. 365–370.
Kanai et al., (1993) FASEB J., 7: 1450–1459.
Kanner, (1993), FEBS Lett., 325 (1,2): pp. 95–99.
Pines et al., (1992) Nature, 360: pp. 464–467.
Schloss et al. (1992) FEBS Lett., 307 (1): pp. 76–80.
Shashidharan et al., (1993), Biochim. Biophys. Acta., 1216: pp. 161–164.
Stelzner et al., (1993) FASEB J., 7(4/part 2): A575.
Storck et al., (1992), Proc. Natl. Acad. Sci., 89: pp. 10955–10959.
Uhl, (1992), Trends in Neurosci., 15(7): 265–268.
Anderson et al., (1989) J. Biol. Chem., 264: pp. 8222–822.
Arriza et al., (1992) J. Neurosci., 12: 4045–4055.
Barish, (1983) J. Physiol., 342: 309–325.
Bertling et al., (1987) Bioscience Reports, 7: 107–112.
Blakely et al., (1991) Anal. Biochem., 194: 302–308.
Bouvier et al., (1992) Nature, 360: 471–474.
Bussolati et al., (1992) J. Biol. Chem., 267: 8330–8335.
Choi et al., (1987) Neurosci., 7: 357–358.
Chomczynski & Sacchi, (1987) Anal. Biochem., 162: 156–159.
Christensen (1990), Physiol. Rev., 70: 43: 77.
Christensen et al., (1967), J. Biol. Chem., 242:5237–5246.
Eisenberg et al., (1984), J. Molec. Biol., 179: 125–142.
Engelke et al., (1992) J. Bacteriol., 171: 5551–5560.
Fairman, (1995) Human Excitatory Amino Acid Transporter 4. Genbank Accession No. U18244.
Felgner et al., (1987) Proc. Natl. Acad. Sci., 84: 7412–7417.
Gerogiou, (1988) AICHE Journal, vol. 34, No. 8, pp. 1233–1248.
Gluzman, (1981) Cell, 23: 175–182.
Guastella et al., (1992) Proc. Natl. Sci., 89: 7189–7193.
Guastella et al., (1990) Science, 249: 1303–1306.
Kanai et al., (1994) J. Biol Chem., vol. 269, No. 32, pp. 20599–20606.
Kanner & Schuldiner, (1987), CRC Crit. Rev. Biochem., 22: 1–38.
Kavanaugh et al., (1992) J. Biol. Chem., 267:22007–22009.
Kim et al., (1991) Nature, 352: 725–728.
Kong et al., (1993) J. Biol. Chem., 268: 1509–1512.
Kozak, (1987) Nucleic Acid Res., 15: 8125–8132.
Maenz et al., (1992), J. Biol. Chem., 267: 1510–1516.
Makowski & Christensen, (1982) J. Biol. Chem., 257: 14635–14638.
Nicholls & Atwell, (1990), TIPS, 11: 462–468.
Olney et al., (1990) Science, 248: 596–599.
Quick and Lester, (1994) Methods in Neuroscience, 19: 261–279.
Saiki et al., (1988) Science, 239: 487–491.
Sanger et al., (1977) Proc. Natl. Acad. Sci., 74: 5463
Smith & Johnson, (1988) Gene, 67: 31–40.
Smithies et al., (1985) Nature, 317:230–234.
Thomas & Capecchi, (1987) Cell, 51: 503–512.
Wallace et al., (1990) J. Bacteriol., 172: 3214–3220.
Wang et al., (1991) Nature, 352: 729–731.
Dreyer et al., (1996) Arch. Ophthalmol., 114: 299–305.
Honda, (1996) Nippon Ganka Gakkst Zasshi, 100: 937–955.
Kalloniatis, (1995) J. Amer. Optom. Assoc., 66: 750–757.
Zerangue et al., (1995) J. Biol. Chem., 270: 6433–6435.
Kataoka et al., (1997) J. Neurosci., 17: 7017–7024.
Sheng et al., (1996) Neuron., 17: 575–578.

*Primary Examiner*—Lisa J. Hobbs
*Attorney, Agent, or Firm*—McDonnell Boehnen Hulbert & Berghoff

[57] ABSTRACT

This invention relates to novel mammalian excitatory amino acid transporter proteins and genes encoding such proteins. The invention is directed towards the isolation, characterization and use of human excitatory amino acid transporter proteins for pharmacological screening of analogues, agonists, antagonists, inhibitors, modulators and facilitators of excitatory amino acid transport in a variety of tissues, particularly neuronal tissues. This invention provides isolated nucleic acid encoding a novel excitatory amino acid transporter subtype that is specifically expressed in retina. Also provided are recombinant expression constructs capable of expressing this novel transporter in transformed prokaryotic and eukaryotic cells, and also provides such transformed cell cultures producing the novel human transporter. Purified transporter protein and membranes comprising the transporter protein are also provided. The invention provides methods of screening compounds in vitro for transporter binding properties using said preparations of protein and membranes from transformed cell cultures, as well as from amphibian oocytes expressing the human transporter protein provided herein.

11 Claims, 7 Drawing Sheets

Figure 1A

```
         10         20         30         40         50         60
          *          *          *          *          *          *
GAATTCGCCGTGTGGCCGCCTTAGAGGGAAGCCACACGGGCATGGCCGTGGGGCTGGCGA 70         80         90        100        110        120
          *          *          *          *          *          *
CTGGTGTTTAGCAACTCCGACCACCTGCCTGCTGAGGGGCTAGAGCCCTCAGCCCAGACC 130        140        150        160        170        180
          *          *          *          *          *          *
CTGTGCCCCGGCCGGGCTCTCATGCGTGGAATGGTGCTGTGCCCCTTGCCAGCAGGCCA 190        200        210        220        230        240
          *          *          *          *          *          *
GGCTCACCATGGTGCCGCATACCATCTTGGCACGGGGGAGGGACGTGTGCAGGCGGAATG
            MetValProHisThrIleLeuAlaArgGlyArgAspValCysArgArgAsn>

250        260        270        280        290        300
          *          *          *          *          *          *
GACTCCTCATCCTGTCTGTGCTGTCTGTCATCGTGGGCTGCCTCCTCGGCTTCTTCTTGA
GlyLeuLeuIleLeuSerValLeuSerValIleValGlyCysLeuLeuGlyPhePheLeu>

310        320        330        340        350        360
          *          *          *          *          *          *
GGACCCGGCGCCTCTCACCACAGGAAATTAGTTACTTCCAGTTCCCCGGAGAGCTCCTGA
ArgThrArgArgLeuSerProGlnGluIleSerTyrPheGlnPheProGlyGluLeuLeu>

370        380        390        400        410        420
          *          *          *          *          *          *
TGAGGATGCTGAAGATGATGATCCTGCCACTGGTGTTCTCCAGCTTGATGTCCGGACTTG
MetArgMetLeuLysMetMetIleLeuProLeuValPheSerSerLeuMetSerGlyLeu>

430        440        450        460        470        480
          *          *          *          *          *          *
CCTCCCTGGATGCCAAGACCTCTAGCCGCCTGGGCGTCCTCACCGTGGCGTACTACCTGT
AlaSerLeuAspAlaLysThrSerSerArgLeuGlyValLeuThrValAlaTyrTyrLeu>

490        500        510        520        530        540
          *          *          *          *          *          *
GGACCACCTTCATGGCTGTCATCGTGGGCATCTTCATGGTCTCCATCATCCACCCAGGCA
TrpThrThrPheMetAlaValIleValGlyIlePheMetValSerIleIleHisProGly>

550        560        570        580        590        600
          *          *          *          *          *          *
GCGCGGCCCAGAAGGAGACCACGGAGCAGAGTGGGAAGCCCATCATGAGCTCAGCCGATG
SerAlaAlaGlnLysGluThrThrGluGlnSerGlyLysProIleMetSerSerAlaAsp>

610        620        630        640        650        660
          *          *          *          *          *          *
CCCTGTTGGACCTCATCCGGAACATGTTCCCAGCCAACCTAGTAGAAGCCACATTCAAAC
AlaLeuLeuAspLeuIleArgAsnMetPheProAlaAsnLeuValGluAlaThrPheLys>

670        680        690        700        710        720
          *          *          *          *          *          *
AGTACCGCACCAAGACCACCCCAGTTGTCAAGTCCCCCAAGGTGGCACCAGAGGAGGCCC
GlnTyrArgThrLysThrThrProValValLysSerProLysValAlaProGluGluAla>

730        740        750        760        770        780
          *          *          *          *          *          *
CTCCTCGGCGGATCCTCATCTACGGGGTCCAGGAGGAGAATGGCTCCCATGTGCAGAACT
ProProArgArgIleLeuIleTyrGlyValGlnGluGluAsnGlySerHisValGlnAsn>
```

Figure 1B

```
          790       800       810       820       830       840
           *         *         *         *         *         *
     TCGCCCTGGACCTGACCCCGCCGCCCGAGGTCGTTTACAAGTCAGAGCCGGGCACCAGCG
     PheAlaLeuAspLeuThrProProProGluValValTyrLysSerGluProGlyThrSer>

850       860       870       880       890       900
           *         *         *         *         *         *
     ATGGCATGAATGTGCTGGGCATCGTCTTCTTCTCTGCCACCATGGGCATCATGCTGGGCC
     AspGlyMetAsnValLeuGlyIleValPhePheSerAlaThrMetGlyIleMetLeuGly>

910       920       930       940       950       960
           *         *         *         *         *         *
     GCATGGGTGACAGCGGGGGCCCCCTGGTCAGCTTCTGCCAGTGCCTCAATGAGTCGGTCA
     ArgMetGlyAspSerGlyGlyProLeuValSerPheCysGlnCysLeuAsnGluSerVal>

970       980       990      1000      1010      1020
           *         *         *         *         *         *
     TGAAGATCGTGGCGGTGGCTGTGTGGTATTTCCCCTTCGGCATTGTGTTCCTCATTGCGG
     MetLysIleValAlaValAlaValTrpTyrPheProPheGlyIleValPheLeuIleAla>

1030      1040      1050      1060      1070      1080
           *         *         *         *         *         *
     GTAAGATCCTGGAGATGGACGACCCCAGGGCCGTCGGCAAGAAGCTGGGCTTCTACTCAG
     GlyLysIleLeuGluMetAspAspProArgAlaValGlyLysLysLeuGlyPheTyrSer>

1090      1100      1110      1120      1130      1140
           *         *         *         *         *         *
     TCACCGTGGTGTGCGGGCTGGTGCTCCACGGGCTCTTTATCCTGCCCCTGCTCTACTTCT
     ValThrValValCysGlyLeuValLeuHisGlyLeuPheIleLeuProLeuLeuTyrPhe>

1150      1160      1170      1180      1190      1200
           *         *         *         *         *         *
     TCATCACCAAGAAGAATCCCATCGTCTTCATCCGCGGCATCCTGCAGGCTCTGCTCATCG
     PheIleThrLysLysAsnProIleValPheIleArgGlyIleLeuGlnAlaLeuLeuIle>

1210      1220      1230      1240      1250      1260
           *         *         *         *         *         *
     CGCTGGCCACCTCCTCCAGCTCAGCCACACTGCCCATCACCTTCAAGTGCCTGCTGGAGA
     AlaLeuAlaThrSerSerSerSerAlaThrLeuProIleThrPheLysCysLeuLeuGlu>

1270      1280      1290      1300      1310      1320
           *         *         *         *         *         *
     ACAACCACATCGACCGGCGCATCGCTCGCTTCGTGCTGCCCGTGGGTGCCACCATCAACA
     AsnAsnHisIleAspArgArgIleAlaArgPheValLeuProValGlyAlaThrIleAsn>

1330      1340      1350      1360      1370      1380
           *         *         *         *         *         *
     TGGACGGCACTGCGCTCTACGAGGCTGTGGCCGCCATCTTCATCGCCCAGGTCAACAACT
     MetAspGlyThrAlaLeuTyrGluAlaValAlaAlaIlePheIleAlaGlnValAsnAsn>

1390      1400      1410      1420      1430      1440
           *         *         *         *         *         *
     ACGAGCTGGACTTTGGCCAGATCATCACCATCAGTATCACAGGCACTGCAGCCAGCATTG
     TyrGluLeuAspPheGlyGlnIleIleThrIleSerIleThrGlyThrAlaAlaSerIle>

1450      1460      1470      1480      1490      1500
           *         *         *         *         *         *
     GGGCAGCTGGCATCCCCCAGGCCGGCCTCGTCACCATGGTCATCGTGCTCACCTCCGTGG
     GlyAlaAlaGlyIleProGlnAlaGlyLeuValThrMetValIleValLeuThrSerVal>
```

Figure 1C

```
         1510       1520       1530       1540       1550       1560
            *          *          *          *          *          *
    GACTGCCCACCGATGACATCACCCTCATCATTGGCGTTGACTGGGCTCTGGACCGTTTCC
    GlyLeuProThrAspAspIleThrLeuIleIleGlyValAspTrpAlaLeuAspArgPhe>

1570       1580       1590       1600       1610       1620
            *          *          *          *          *          *
    GCACCATGATTAACGTGCTGGGTGATGCGCTGGCAGCGGGGATCATGGCCCATATATGTC
    ArgThrMetIleAsnValLeuGlyAspAlaLeuAlaAlaGlyIleMetAlaHisIleCys>

1630       1640       1650       1660       1670       1680
            *          *          *          *          *          *
    GGAAGGATTTTGCCCGGGACACAGGCACCGAGAAACTGCTGCCCTGCGAGACCAAGCCAG
    ArgLysAspPheAlaArgAspThrGlyThrGluLysLeuLeuProCysGluThrLysPro>

1690       1700       1710       1720       1730       1740
            *          *          *          *          *          *
    TGAGCCTCCAGGAGATCGTGGCAGCCCAGCAGAATGGCTGTGTGAAGAGTGTAGCCGAGG
    ValSerLeuGlnGluIleValAlaAlaGlnGlnAsnGlyCysValLysSerValAlaGlu>

1750       1760       1770       1780       1790       1800
            *          *          *          *          *          *
    CCTCCGAGCTCACCCTGGGCCCCACCTGCCCCCACCACGTCCCCGTTCAAGTGGAGCGGG
    AlaSerGluLeuThrLeuGlyProThrCysProHisHisValProValGlnValGluArg>

1810       1820       1830       1840       1850       1860
            *          *          *          *          *          *
    ATGAGGAGCTGCCCGCTGCGAGTCTGAACCACTGCACCATCCAGATCAGCGAGCTGGAGA
    AspGluGluLeuProAlaAlaSerLeuAsnHisCysThrIleGlnIleSerGluLeuGlu>

1870       1880       1890       1900       1910       1920
            *          *          *          *          *          *
    CCAATGTCTGAGCCTGCGGAGCTGCAGGGGCAGGCGAGGCCTCCAGGGGCAGGGTCCTGA
    ThrAsnVal***>

1930       1940       1950       1960       1970       1980
            *          *          *          *          *          *
    GGCAGGAACTCGACTCTCCAACCCTCCTGAGCAGCCGGTAGGGGCAGGATCACACATTC 1990       2000       2010       2020       2030       2040
            *          *          *          *          *          *
    TTCTCACCCTTGAGAGGNTGGAATTAACCCCGCTTGGACGGAAAATGTNTCTCAAGAGAA 2050       2060       2070       2080       2090       2100
            *          *          *          *          *          *
    GGGAAAGGNTGCATGGGGGAGCCCATCCAGGGAGTGATGGGCCCGGATTGGCTGANGGCC 2110       2120       2130       2140       2150       2160
            *          *          *          *          *          *
    CNTTGTGAAAGTTTCCCCCGTNGTGAACCCCGGTGAAGGGGGGAAGGCAGGGGGTTTTCC 2170       2180       2190
            *          *          *
    GGCCCCCCTTTTCTTGGATGANAGGATTTGGACC
```

Figure 2

EXCITATORY AMINO ACID TRANSPORTER GENE AND USES

This application is a divisional of U.S. Ser. No. 08/948,569, filed Oct. 10, 1997, now U.S. Pat. No. 5,882,926, which is a continuation of U.S. Ser. No. 60/028,325, filed Oct. 11, 1996, which is a Provisional application of U.S. Ser. No. 08/140,729, filed Oct. 20, 1993, now U.S. Pat. No. 5,658,782, issued Aug. 19, 1997. The disclosures of each of these prior applications are considered as being part of the disclosure of the application and are explicitly incorporated by reference herein.

This invention was made with government support under National Institute of Health grant DA07595. The government has certain rights to this invention.

BACKGROUND OF THE INVENTION

1. Field of the Invention

This invention relates to amino transporters from mammalian species and the genes corresponding to such transporters. Specifically, the invention relates to the isolation, cloning and sequencing of complementary DNA (cDNA) copies of messenger RNA (mRNA) encoding a novel human amino acid transporter gene. The invention also relates to the construction of recombinant expression constructs comprising such cDNAs from a novel human amino acid transporter gene of the invention, said recombinant expression constructs being capable of expressing amino acid transporter protein in cultures of transformed prokaryotic and eukaryotic cells as well as in amphibian oocytes. Production of the transporter protein of the invention in such cultures and oocytes is also provided. The invention relates to the use of cultures of such transformed cells to produce homogeneous compositions of the novel transporter protein. The invention also provides cultures of such cells and oocytes expressing transporter protein for the characterization of novel and useful drugs. Antibodies against and epitopes of the transporter protein are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organism such as man. For these reasons, specialized trans-membrane transporter proteins have evolved in all organisms to recover or scavenge extracellular amino acids (see Christensen, 1990, Physiol. Rev. 70: 43–77 for review).

These transporter proteins play a particularly important role in uptake of extracellular amino acids in the vertebrate brain and peripheral motor and sensory tissues (see Nicholls & Attwell, 1990, TiPS 11: 462–468). Amino acids that function as neurotransmitters must be scavenged form the synaptic cleft between neurons to enable continuous repetitive synaptic transmission. More importantly, it has been found that high extracellular concentrations of certain amino acids (including glutamate and cysteine) can cause neuronal cell death. High exti-acellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS: see Pines et al., 1992 Nature 360: 464–467).

Glutamate is one example of such amino acid. Glutamate is an excitalory neurotransmitter (i.e., excitatory neurons use glutamate as a neurotransmitter). When present in excess (>about 300 μM; Bouvier et al., 1992, Nature 360: 471–474; Nicholls & Attwell, ibid., >5 μM for 5 min.; Choi et al., 1987, J. Neurosci. 7: 357–358), extracellular glutamate causes neuronal cell death. Glutamate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather that decreasing the amount of extracellular glutamate found in the brain. The resulting high extracellular concentration of glutamate causes neuron death, with extremely deleterious consequences for motor and other brain functions, resulting in stroke and other instances of organic brain dysfunction.

This important role for amino acid transporters in maintaining brain homeostasis of extracellular amino acid concentrations has provided the impetus for the search for an development of compounds to modulate and control transporter function. However, conventional screening methods require the use of animal brain slices in binding assays as a first step. This is suboptimal for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. These same limitations arise in the use of animal-derived sensory tissue, particularly retina, to study the effects of transporter function in these tissues. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, J. Biol. Chem. 242: 5237–5246 report the discovery of a neutral amino acid transporter (termed the ACS transporter) in Erlich ascites tumor cells.

Makowske & Christensen, 1982, J. Biol Chem. 257: 14635–14638 provide a biochemical characterization of hepatic amino acid transport.

Kanner & Schuldiner, 1987, CRC Crit. Rev. Biochem. 22: 1–38 provide a review of the biochemistry of neurotransmitters.

Olney et al., 1990 Science 248: 596–599 disclose that the amino acid cysteine is a neurotoxin when present in excess extracellularly.

Wallace et al., 1990, J. Bacteriol. 172: 3214–3220 report the cloning and sequencing of a glutamate/aspartate transporter gene termed gltP from Escherichia coli strain K12.

Kim et al., 1991, Nature 352: 725–728 report the discovery that a cationic amino acid transporter is the cell surface target for infection by ecotropic retroviruses in mice.

Wang et al., 1991, Nature 352: 729–731 report the discovery that a cationic amino acid transporter is the cell surface target for infection by ecotropic retroviruses in mice.

Maenz et al., 1992, J. Biol Chem. 267: 8330–8335 report that the ASC transporter acts in a electrochemically neutral manner so that sodium ion co-transport occurs without disrupting the normal membrane potential of the cells expressing the transporter.

Engelke et al., 1992, *J. Bacteriol.* 171: 5551–5560 report cloning of a dicarboxylate carrier from *Rhizobium meliloti.*

Guastella et al., 1992, *Proc. Natl. Acad. Sci.* USA 89: 7189–7193 disclose the cloning of a sodium ion and chloride ion-dependent glycine transporter from a glioma cell line that is expressed in the rat forebrain and cerebellum.

Kavanaugh et al., 1992, *J. Biol Chem.* 267: 22007–22009 report that biochemical characterization of a rat brain GABA transporter expressed in vitro in *Xenopus laevis* oocytes.

Storck et al., 1992, *Proc. Natl. Acad. Sci.* USA 89: 10955–10959 disclose the cloning and sequencing of a sodium ion-dependent glutamate/aspartate transporter from rat brain termed GLAST1.

Bouvier et al., ibid., disclose the biochemical characterization of a glial cell-derived glutamate transporter.

Pines et al., ibid., report the cloning and sequencing of a glial cell glutamate transporter from rat brain termed GLT-1.

Kanai & Hediger, 1992, *Nature* 360: 467–471 disclose the cloning and sequence of a sodium ion-dependent neutral amino acid transporter of the A type that is homologous to a sodium-ion dependent glucose transporter.

Arriza et al., 1994, *J. Neurosci.* 14: 5559–5569 disclose genes for three novel glutamate transporters.

Nicholls & Attwell, ibid., review the role of amino acids and amino acid transporters in normal and pathological brain functions.

In humans, the sodium-dependent glutamate uptake transporters include 4 known subtypes, termed EAAT1 through EAAT3, that are expressed in neurons in the brain, as disclosed in co-owned and co-pending U.S. Ser. No. 08/140,729, filed Oct. 23, 1993, low U.S. Pat. No. 5,658,782, issued Aug. 19, 1997, and EAAT4, that are expressed in neurons in the cerebellum, as disclosed in co-owned and co-pending U.S. Ser. No. 08/663,808, filed Jun. 14, 1996, the disclosures of each of which are incorporated by reference herein. The transport of glutamate is driven by the co-transport of sodium ions and counter-transport of potassium ions down their electrochemical gradients across mammalian cell membranes, and may also involve co-transport of a proton. In addition, glutamate transport is also associated with uncoupled, passive efflux of chloride ions, the relative magnitude of such efflux varying with EAAT subtype. For EAAT1 through EAAT3, the magnitude of the chloride conductance is similar or smaller than the electrogenic transport current; for EAAT4, on the other hand, the (current generated in experimental systems using *Xenopus laevis* oocytes is almost entirely due to chloride ion flux.

A chloride ion current associated with glutamate transporter activity has also been observed in retina, specifically retinal cone and rod photoreceptor cells and bipolar cells. As in central nervous system tissues, glutamate transport may play an important role in several neurological diseases that occur in the eye. Excessive levels of glutamate are neurotoxic and may be responsible for damage to retinal neurons due to glaucoma (Dreyer et al., 1996, *Arch. Ophthalmol.* 114: 299–305) and retinal ischemia (Honda, 1996, *Nippon Ganka Gakkat Zasshi* 100: 937–955), as well as retinopathy associated with premature birth, hypertension and diabetes (Kalloniatis, 1995, *J. Amer. Optom. Assoc.* 66: 750–757). Up-regulation of glutamate transport could be neuroprotective by lowering extracellular levels of glutamate in retina; pharmacological regulation of glutamate transporters has been demonstrated in frog oocytes (Zerangue et al., 1995, *J. Biol. Chem.* 270: 6433–6435) and native cells (Kataoka et al., 1997, *J. Neurosci.* 17: 7017–7024). Thus, there is a need in the art to determine the basis of the chloride ion current in retinal tissues and to determine whether the activity of a EAAT transporter is involved, in order to develop retinal protective agents for a variety of diseases and disorders.

SUMMARY OF THE INVENTION

The present invention relates to the cloning, expression and functional characterization of mammalian excitatory amino acid transporter genes. The invention comprises nucleic acids having a nucleotide sequence of a novel excitatory amino acid transporter gene. The nucleic acids provided by the invention each comprise a complementary DNA (cDNA) copy of the corresponding mRNA transcribed in vivo from the excitatory amino acid transporter gene of the invertion. Also provided is the deduced amino acid sequences of the cognate protein of the cDNA provided by the invention.

This invention provides nucleic acids, nucleic acid hybridization probes, recombinant eukaryotic expression constructs capable of expressing the excitatory amino acid transporter of the invention in cultures of transformed cells and in amphibian oocytes, such as cultures of transformed eukaryotic cells and such amphibian oocytes that synthesize the excitatory amino acid transporter of the invention, and a homogeneous composition of the excitatory amino acid transporter protein of the invention. Methods for characterizing this transporter protein and methods for using this protein and cells and oocytes expressing this protein for the development of agents having pharmacological uses related to this transporter protein are also provided by the invention.

In a first aspect, the invention provides a nucleic acid having a nucleotide sequence encoding a human excitatory amino acid transporter that is the EAAT5 transporter. In this embodiment of the invention, the nucleic acid encodes an amino acid sequence of 560 amino acid residues identified as SEQ ID No.: 10. In a preferred embodiment, the nucleotide sequence includes 2194 nucleotides of the human EAAT5 cDNA comprising 1680 nucleotides of coding sequence, 188 nucleotides of 5' untranslated sequence and 326 nucleotides of 3' untranslated sequence, identified as SEQ ID No.: 9. A preferred embodiment of the EAAT5 transporter is the nucleotide sequence depicted in FIGS. 1A through 1C (SEQ ID No: 9).

In another aspect, the invention comprises a homogeneous composition of the 61 kilodalton (kD) mammalian EAAT5 transporter and derivatives thereof, said size being understood to be the size of the protein before any post-translational modifications thereof. The amino acid sequence of the EAAT5 transporter and derivatives thereof preferably is the amino acid sequence of the human EAAT5 transporter protein shown in FIGS. 1A through 1C (SEQ ID No: 10). EAAT5 protein molecules provided by the invention are understood to have substantially the same biological properties as the EAAT5 protein molecule encoded by the nucleotide sequence described herein. Also provided by the invention are cell membrane preparations, preferably mammalian and amphibian cell membrane preparations, comprising the EAAT5 protein of the invention.

This invention provides both nucleotide and amino acid probes derived from the sequences herein provided. This invention includes probes isolated from either cDNA or genomic DNA, as well as probes made synthetically with the sequence information derived therefrom. The invention specifically included but is no limited to oligonucleotide, nicktranslated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of this transporter gene in various tissues of mammals, including hurnan. It is also an object of the present invention to provide nucleic acid hybridization probes derived from the sequences of the excitatory amino acid transporter gene of the invention to be used for the detection and diagnosis of genetic diseases. It is an object of this invention to provide nucleic acid hybridization probes derived from the DNA sequence of the excitatory amino acid transporter gene herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of excitatory amino acid transporter-specific antibodies, or used for competitors of excitatory amino acid transporter molecules for amino acid, agonist, antagonist or drug binding, or to be used for the production of inhibitors of the binding of agonist or antagonists or analogues thereof to such excitatory amino acid transporter molecules.

The present invention also provides antibodies against and epitopes of the mammalian amino acid transporter molecules of the invention. It is an object of the present invention to provide antibodies that are immunologically reactive to the excitatory amino acid transporters of the invention. It is a particular object to provide monoclonal antibodies against this excitatory amino acid transporter, most preferably the human excitatory amino acid transporter as herein disclosed. Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with a cell line which expresses antigens or epitopes of an excitatory amino acid transporter of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the excitatory amino acid transporter of the invention. Chimeric antibodies immunologically reactive against the excitatory amino acid transporter protein of the invention are also within the scope of this invention.

The present invention provides recombinant expression constructs comprising a nucleic acid encoding an excitatory amino acid transporter of the invention wherein the construct is capable of expressing the encoded excitatory amino acid transporter in cells, preferably mammalian or amphibian cells, and most preferably in mammalian cell culture transformed with the construct or amphibian oocytes comprising excitatory amino acid-encoding mRNA. Preferred embodiments of such constructs comprise a cDNA encoding a mammalian EAAT5 protein having an amino acid sequence identified as SEQ ID No.: 10. In other preferred embodiments, the cDNA encodes human EAAT5, most preferably having a nucleic acid sequence identified as SEQ ID No.: 9. The recombinant expression constructs provided by the invention are capable of expressing the excitatory amino acid transporter encoded therein in cells and oocytes transformed with the construct or into which the construct has otherwise been introduced.

The invention also provides cell cultures transformed with the recombinant expression constructs of the invention, each such culture being capable of and expressing the excitatory amino acid transporter encoded in the transforming construct. The invention also provides amphibian oocytes into which a recombinant expression construct of the invention is introduced, each such oocyte being capable of and expressing the excitatory amino acid transporter encoded in the transforming construct, or wherein RNA, most preferably mRNA, encoding the excitatory amino acid transporter protein has been introduced.

The present invention also includes within its scope protein preparations of prokaryotic and eukaryotic cell membranes containing the amino acid transporter protein of the invention, derived from cultures of prokaryotic or eukaryotic cells, respectively, transformed with the recombinant expression constructs of the invention. In a preferred embodiment, such preparation of cell membranes comprise the excitatory amino acid transporter proteins of the invention.

The invention also provides methods for screening compounds for their ability to inhibit, facilitate or modulate the biochemical activity of the excitatory amino acid transporter molecules of the invention, for use in the in vitro screening of novel agonist and antagonist compounds. In preferred embodiments, cells, particularly amphibian oocytes comprising nucleic acid encoding a mammalian excitatory amino acid transporter protein of the invention, including recombinant expression constructs of the invention, are contacted with such a compound, and the effect of the compound on excitatory amino acid transport is assayed. In preferred embodiments, transported amino acids include glutamate and aspartate, most preferably L-glutamate. Additional preferred embodiments comprise quantitative analyses of such effects. Also provided are assays that distinguish between the effects of such compounds on excitatory amino acid transport from effects of such compounds on chloride ion transport by the excitatory amino acid transporters of the invention.

The present invention is also useful for the detection of analogues, agonists or antagonists, heretofore known or unknown, of the excitatory amino acid transporters of the invention, either naturally occurring or embodied as a drug. In preferred embodiments, such analogues, agonists or antagonists may be detected in blood, saliva, semen, cerebrospinal fluid, plasma, lymph, vitreous humor, or any other bodily fluid. In additional preferred embodiments, the invention provides methods for detecting and identifying analogues, agonists or antagonists that preferentially affect either the amino acid uptake function or the chloride ion channel function of the amino acid transporters of the invention.

Specific preferred embodiments of the present invention will become evident from the following more detailed description of certain preferred embodiments and the claims.

DESCRIPTION OF THE DRAWINGS

FIGS. 1A through 1C illustrate the nucleotide (SEQ ID No.: 9) and amino acid (SEQ ID No.: 10) sequence of the human EAAT5 excitatory amino acid transporter.

FIG. 2 presents an amino acid sequence comparison between human EAAT5 (SEQ ID No.: 10) and the excitatory amino acid transporters EAAT1 (SEQ ID No.: 2), EAAT2

(SEQ ID No.: 4), EAAT3 (SEQ ID No.: 6) and EAAT4 (SEQ ID No.: 8), wherein amino acid residues identical in 4 of 5 transporters are shown in white-on-black lettering. Also shown is one potential version of the transmembrane topology of the transporters, where (i-o) indicates that the sequence segment is arrayed from the inside to the outside of the cell, and (o-i) indicates that the sequence segment is arrayed from the outside to the inside of the cell across the cell membrane. Eight transmembrane segments (termed I through VIII) are shown.

Figure 3:
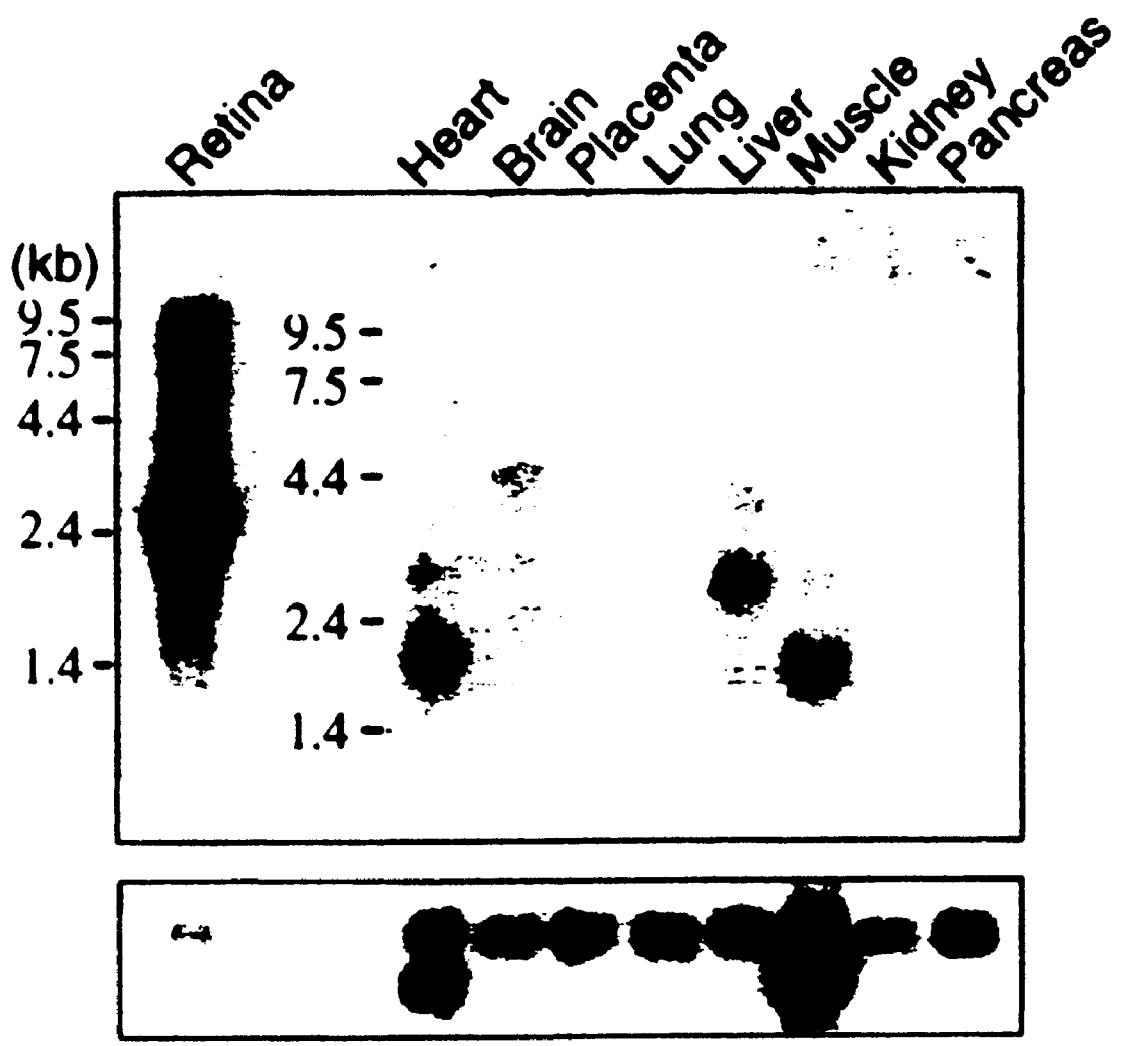

FIG. 3 is an autoradiograph of niRNA from retina and other tissues hybridized with a EAAT5 specific probe and illustrating retinal-specific expression of EAAT5 in human tissues. The bottom portion of the Figure shows the same filter stripped of EAAT5 probe and re-hybridized with a β-actin probe as a control for mRNA loading in each lane.

FIGS. 4A through 4D illustrate the results of functional assays performed using *Xenopus laevis* oocytes injected with and expressing EAAT5 mRNA.

Figure 4B:
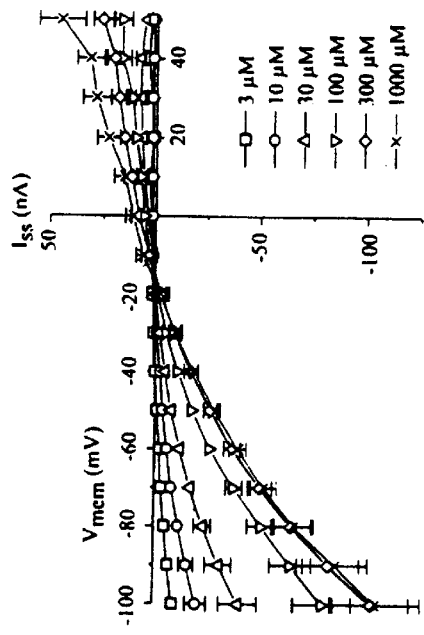
Figure 4D:
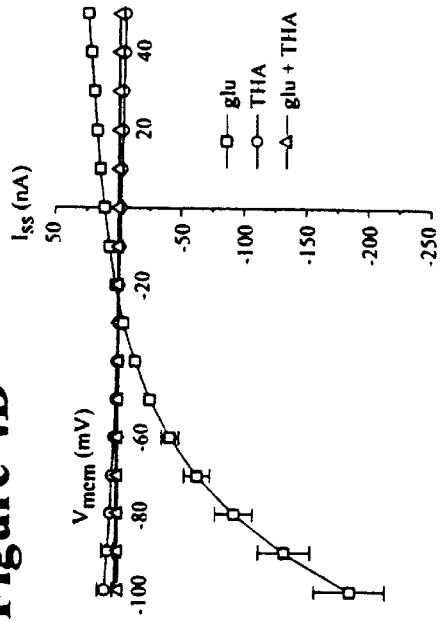
Figure 4A:
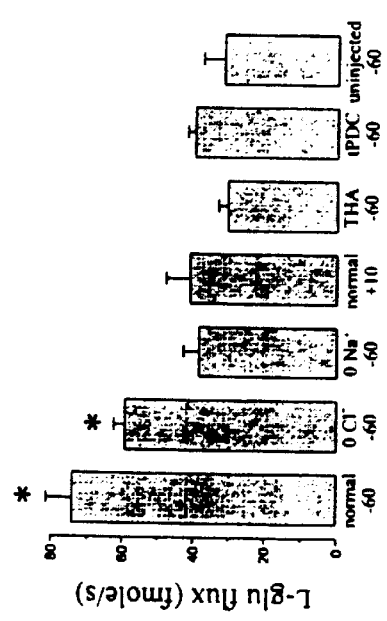

FIG. 4A shows the amount of ($^3$H)-glutamate uptake in oocytes voltage-clamped at −60 mV (−60) or +10 mV (+10) in normal Ringers solution (normal), sodium-free (0 Na$^+$) or chloride-free (0 Cl$^-$) Ringers solution, or in the presence of threo-β-hydroxyaspartate (THA) or L-trans-pyrollidine-2,4-dicarboxylic acid (tPDC), or uninjected (uninjected).

FIG. 4B is a graph of the L-glutamate dose- and voltage-dependent steady-state current elicited by application of L-glutamate to EAAT5-expressing oocytes (data averaged from 7 cells). L-glutamate was applied in the following concentrations: -□-=3 μM; -○-=10 μM; -Δ-=30 μM; -∇-= 100 μM; -◇-=300 μM; -x-=1000μM.

Figure 4C:
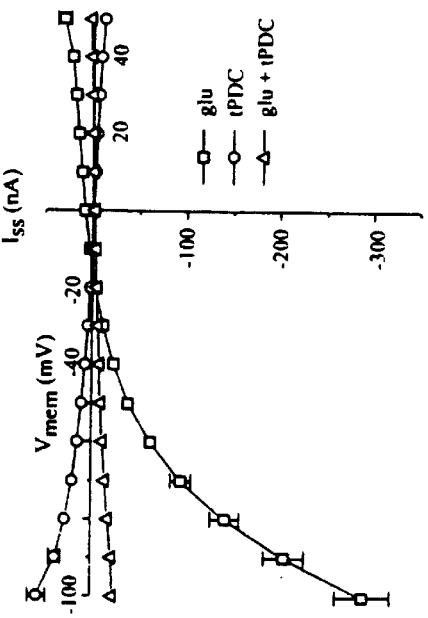

FIG. 4C is a graph of the steady-state current elicited by application of 100 μM L-glutamate alone to Xenopus oocytes expressing human EAAT5 (shown as -□-) or in the presence of 100 μM tPDC (-Δ-), showing that tPDC blocks the L-glutamate induced steady state current. Application of 100 μm tPDC alone (-○-) elicited a small, outward current at hyperpolarized potentials.

FIG. 4D is a graph of the steady-state current elicited by application of 100 μM L-glutamate alone to Xenopus oocytes expressing human EAAT5 (shown as -□-) or in the presence of 100 μM THA (-Δ-), showing that THA blocks the L-glutamate induced steady state current. Application of 100 μm THA alone (-○-) elicited a small, outward current at hyperpolarized potentials.

FIGS. 5A through 5D illustrate the ion dependence of EAAT5 mediated currents induced in Xenopus oocytes expressing human EAAT5.

Figure 5B:
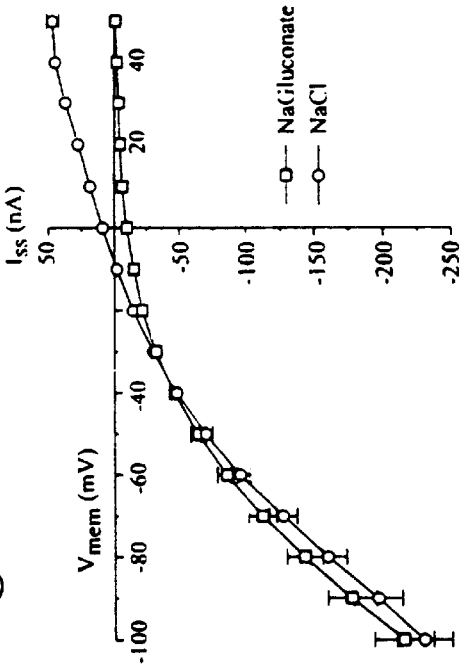
Figure 5D:
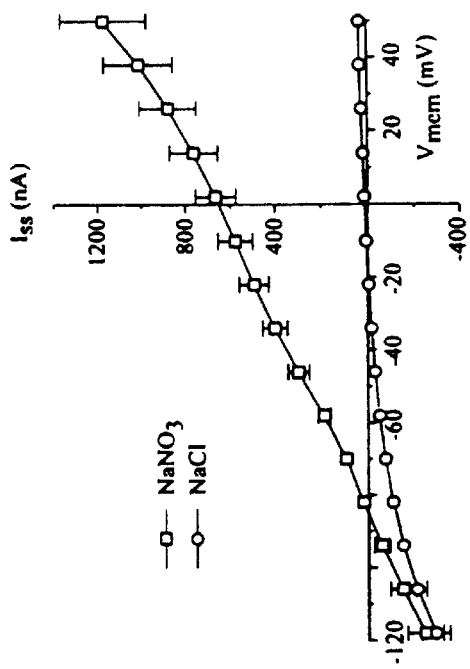
Figure 5A:
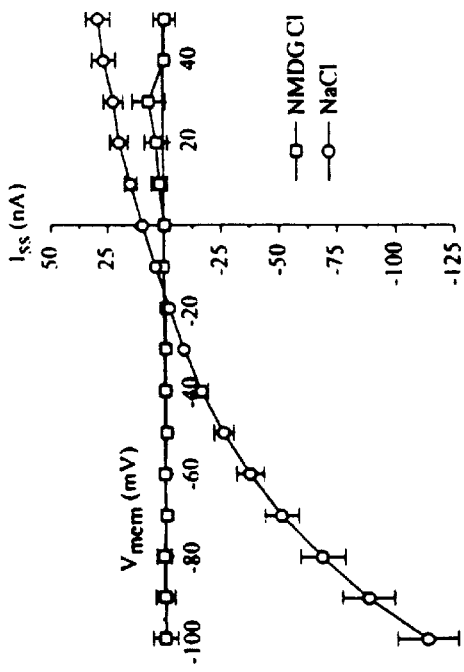

FIG. 5A is a graph of the steady-state current elicited by application of 100 μM L-glutamate alone to Xenopus oocytes expressing human EAAT5 in normal Ringers solution (shown as -○-) or in Ringers solution where sodium ions have been replaced by N-methyl D-glucamine (-□-), showing that this replacement abolishes the L-glutamine induced current.

FIG. 5B is a graph of the steady-state current elicited by application of 100 μM L-glutamate alone to Xenopus oocytes expressing human EAAT5 in normal Ringers solution (shown as -○-) or in Ringers solution where chloride ions have been replaced by gluconate (-□-), showing that this replacement has no effect at negative potentials but blocks outward current at positive potentials.

Figure 5C:
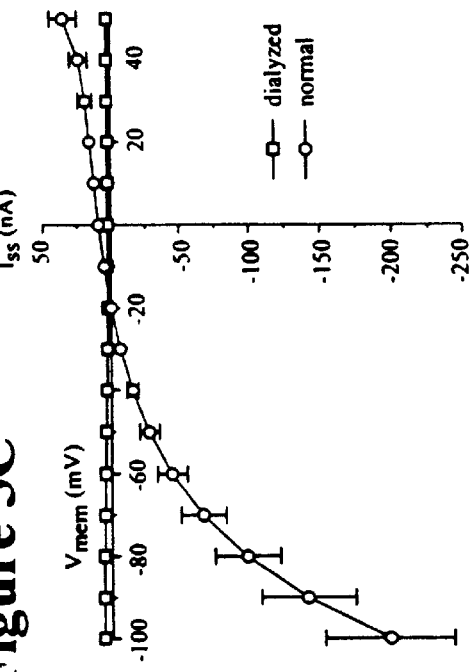

FIG. 5C is a graph of the steady-state current elicited by application of 100 μM L-glutamate alone to undialyzed Xenopus oocytes expressing human EAAT5 (shown as -○-) or in oocytes having been dialyzed in chloride-free solution for>48 hours (-□-), showing that this replacement abolishes the L-glutamine induced current.

FIG. 5D is a graph of the steady-state current elicited by application of 100 μM L-glutamate alone to Xenopus oocytes expressing human EAAT5 in normal Ringers solution (shown as -○-) or in Ringers solution where chloride ions have been replaced by nitrate (-□-), showing that this replacement elicits a large outward current.

DETAILED DESCRIPTION OF THE PREFERRED EMBODIMENTS

The term "excitatory amino acid transporter EAAT5" as used herein refers to protein having substantially the same biological activity as the protein having the amino acid sequence depicted in FIGS. 1A through 1C (SEQ ID No.: 10). This definition is intended to encompass alielic variations in the EAAT5 sequence and conservative amino acid substitution variants, either naturally occurring or the product of in vitro chemical or genetic modification, provided that the biochemical properties of the EAAT5 protein as disclosed herein are not substantially or materially affected. Each such variant will be understood to have essentially the same biochemical activity and amino acid sequence as the amino acid sequence of the corresponding EAAT5 protein disclosed herein.

The EAAT5 protein of the invention is encoded by an isolated nucleic acid, most preferably a nucleic acid sequence cloned into a replicable vector using vectors and methods known in the art. Cloned nucleic acid provided by the present invention may encode EAAT5 protein of any species of origin, including, for example, mouse, rat, rabbit, cat, and human, but preferably the nucleic acid provided by the invention encodes EAAT5 receptor of mammalian, most preferably human, origin.

The term "excitatory amino acid" is intended to encompass naturally-occurring and synthetic amino acids such as L-aspartate and L-glutamate, as well as homologues, analogues or derivatives thereof. The terms is also intended to encompass agonists, antagonist and inhibitors of mammalian glutamate and other excitatory amino acid transporters and receptors.

The term "detectably labeled" is intended to encompass any reporter molecule capable of being detected by radioactive, fluorescent, spectrophotometric or other physical or chemical means. Particular examples include radiolabels, including but not limited to $^3$H and $^{14}$C.

The term "chloride equilibrium potential" is intended to mean the membrane potential at which there is no detectable chloride ion flux across the cell membrane.

The nucleic acid hybridization probes provided by the invention comprise DNA or RNA having the nucleotide sequence of the amino acid transporters, depicted in FIGS. 1A through 1C (SEQ ID No.: 9), or any portion thereof effective in nucleic acid hybridization under stringency conditions sufficient to permit specific hybridization of the probe to a complementary nucleic acid sequence. Mixtures of such nucleic acid hybridization probes are also within the scope of this embodiment of the invention. Nucleic acid probes as provided herein are usefil for detecting novel excitatory amino acid transporter genes related to the EAAT5 gene disclosed herein, specifically including homologous, cognate or syntenic transporter genes in non-human mammalian species. Nucleic acid probes as provided herein are also useful for detecting excitatory amino acid transporter gene expression in cells and tissues using techniques well-known in the art, including but not limited to Northern blot hybridization, in situ hybridization and Southern hybridization to reverse transcriptase—polymerase chain reaction (RT-PCR) product DNAs. The probes provided by the present invention, including oligonucleotides probes derived therefrom, are also useful for Southern hybridization of mammalian, preferably human, genomic DNA for screening restriction fragment length polymorphism (RFLP) associated with genetic disorders.

The production of proteins such as excitatory amino acid transporter molecules from cloned genes by genetic engineering means is well known in this art. This discussion which follows is accordingly intended as an overview of this field, and in not intended to reflect the full state of the art.

DNA encoding an excitatory amino acid transporter may be obtained, in view of the instant disclosure, by chemical synthesis, by screening reverse transcripts of mRNA from appropriate cells or cultured cell lines, by screening genomic libraries from appropriate cells or tissues, or by combinations of these procedures, as illustrated below. Screening of mRNA or genomic DNA may be carried out with oligonucleotide probes generated from the nucleic acid sequence information from the excitatory amino acid transporters disclosed herein. Probes may be labeled with a detectable group such as a fluorescent group, a radioactive atom or a chemiluminescent group in accordance with know procedures and used in conventional hybridization assays, as described. Nucleic acid sequences may be obtained by use of the polymerase chain react ion (PCR) procedure, using PCR oligonucleotide primers corresponding to nucleic acid sequence information derived from an excitatory amino acid transporter as provided herein. See U.S. Pat. Nos. 4,683,195 to Mullis et al. and 4,683,202 to Mullis.

The excitatory amino acid transporter protein of the invention may be synthesized in host cells transformed with a recombinant expression construct comprising a nucleic acid encoding excitatory amino acid transporter cDNA. Alternatively, the excitatory amino acid transporter proteins of the invention can be synthesized in amphibian oocytes comprising nucleic acid, preferably mRNA, encoding the excitatory amino acid transporter. Recombinant expression constructs provided by the invention can also be advantageously comprised of a vector that is a replicable DNA construct. Vectors are used herein either to amplify DNA encoding an excitatory amino acid transporter and/or to express DNA encoding an excitatory amino acid transporter gene. For the purposes of this invention, a recombinant expression construct is a replicable DNA construct in which a nucleic acid encoding an excitatory amino acid transporter is operably linked to suitable control sequences capable of effecting the expression of the excitatory amino acid transporter in a suitable host or host cell.

The need for such control sequences will vary depending upon the host selected and the transformation method chosen. Generally, control sequences include a transcriptional promoter, optional ancillary transcription control sequences, such as transcription factor binding domains, enhancer sequences, and other eukaryotic "operator" sequences to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformrants. See, Sambrook et al., : 1990, *Molecular Cloning: A Laboratory Manual* (Cold Spring Harbor Press: New York).

Vectors useful for practicing the present invention include plasmids, viruses (including phage), retroviruses, and integratible DNA fragments (i.e., fragments integratible into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, *J. Biol. Chem.* 264: 8222–8229). Transformed host cells are cells which have been transformed or transfected with recombinant expression constructs made using recombinant DNA techniques and comprising nucleic acid encoding an amino acid transporter protein. In addition, preferred vectors comprise control sequences for in vitro RNA synthesis, whereby RNA prepared in vitro is introduced into the appropriate host cell and excitatory amino acid transporter protein is produced thereby. Preferred host cells are *Xenopus laevis* oocytes, oocytes from other amphibian species, and COS-7 cells (Gluzman, 1981, *Cell* 23: 175–182). Transformed host cells may express the excitatory amino acid transporter protein, but host cells transformed for purposes of cloning or amplifying nucleic acid hybridization probe DNA need not express the transporter. When expressed, the excitatory amino acid transporter protein molecules of the invention will typically be located in the host cell membrane. See, Sambrook et al., ibid.

Cultures of cells derived from multicellular organisms are a desirable lost for recombinant excitatory amino acid transporter protein synthesis. In principal, any higher eukaryotic cell culture is useful, whether from vertebrae or invertebrate culture. However, mammalian cells are preferred, as illustrated in the Examples. Propagation of such cells in cell culture has become a routine procedure. See Tissue Culture, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. COS-7 cells are preferred.

Certain other primary host cells, not subjected to prolonged tissue culture adaptation, can be used to produce the excitory amino acid transporter of the invention, particularly amphibian oocytes. Amphibian oocytes are useful for expressing the mammalian amino acid excitatory transporters of this invention, most preferably ooyctes from *Xenopus laevis* or other amphibian, which oocytes are used to provide cells convenient foe the practice of some of the inventive methods disclosed herein. In these embodiments, the nucleic acid encoding the excitatory amino acid transporter proteins of the invention is preferably RNA, more preferably mRNA, and most preferably in vitro synthesized mRNA as disclosed herein.

Thus, the invention also provides a method for making the mammalian excitatory amino acid transporters of the invention, most preferably human EAAT5, and membrane preparations comprising this transporter, by introducing nucleic acid encoding the transporter into an appropriate prokaryotic, or preferably, eukaryotic, most preferably mammalian, cell that is capable of expressing the transporter protein.

The invention provides homogeneous compositions of the EAAT5 proteins produced by transformed eukaryotic cells as provided herein. Such a homogeneous compositions are intended to be comprised of the corresponding excitatory amino acid transporter protein that comprises at least 50–90% of the protein in such a homogenous composition. The invention also provides membrane preparations from cells expressing the excitatory amino acid transporter protein as the result of transformation with a recombinant expression construct, as described herein.

Amino acid transporter protein made from cloned genes in accordance with the present invention may be use for screening amino acid analogues, or inhibitors, agonists or antagonists of amino acid transport, or for determining the amount of such agonists or antagonists in a solution of interest (e.g. blood plasma or serum). For example, host cells may be transformed with a recombinant expression construct of the present invention, an excitatory amino acid transporter expressed in those host cells, and the cells or membranes thereof used to screen compounds for their effect on excitatory amino acid transport activity. By selection of host cells that do not ordinarily express an excitatory amino acid transporter, pure preparations of membranes containing the transporter can be obtained.

The recombinant expression constructs of the present invention are useful in molecular biology to transform cells which do not ordinarily express a excitatory amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, *Cell* 51: 503–512; Bertling, 1987, *Bioscience Reports* 7: 107–112; Smithies et al., 1985, *Nature* 317: 230–234.

In preferred embodiments, the electrochemistry of the EAAT5 proteins; of the invention are analyzed, and analogues, agonists and antagonists assayed, using amphibian oocytes, most preferably *Xenopus laevis* oocytes, comprising a nucleic acid encoding the excitatory amino acid transporter proteins of the invention that is preferably RNA, more preferably mRNA, and most preferably in vitro synthesized mRNA as disclosed herein, wherein the excitatory amino acid transporter protein of the invention is expressed thereby in the cell membranes of the oocytes. Preferred electrochemical assays are performed as disclosed herein in the Examples set out below.

Oligonucleotides of the present invention are useful as diagnostic tools for probing excitatory amino acid transporter gene expression in tissues of humans and other animals. For example, tissues are probed in situ with oligonucleotide probes carrying detectable groups by conventional autoradiographic techniques, to investigate native expression of this transporter or pathological conditions related thereto.

The invention also provides antibodies that are immunologically reactive to the excitatory amino acid transporter protein or epitopes thereof provided by the invention. The antibodies provided by the invention may be raised, using methods well known in the art, in animals by inoculation with cells that express an excitatory amino acid transporter of the invention or epitopes thereof, cell membranes from such cells, whether crude membrane preparations or membranes purified using methods well known in the art, or purified preparations of proteins, including fusion proteins, particularly fusion proteins comprising epitopes of the excitatory amino acid transporter protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamster, goats and primates. Preferred animals for inoculation are rodents (including mice, rats, hamsters) and rabbits. The most preferred animal is the mouse.

Cells that can be used for such inoculations, or for any of the other means used in the invention, include any cell line that expresses the excitatory amino acid transporter proteins of the invention, or any epitope thereof, as a result of a molecular or genetic engineering, or that has been treated to increase the expression of an endogenous or heterologous excitatory amino acid transporter protein by physical, biochemical or genetic means. Preferred cells are cells expressing the EAAT5 protein of the invention, including mammalian, insect and amphibian cells, and most preferably cells syngeneic to the animal to be inoculated, that have been transformed with a recombinant expression construct of the invention encoding an excitatory amino acid transporter protein, and that express the transporter therefrom.

The present invention also provides monoclonal antibodies that are immunologically reactive with an epitope derived from an excitatory amino acid transporter of the invention, or fragment thereof, present on the surface of such cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cell of a myeloma cell line with spleen cells derived from animals immunized with cells expressing an excitatory amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line in P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supematarit fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an excitatory amino acid transporter of the invention. The present invention also encompasses fragments, including but not limited to F(ab), F(ab)' and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an excitatory amino acid transporter of the invention, made by methods known to those of skill in the art.

The present invention also encompasses an epitope of an excitatory amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an excitatory amino acid transporter-derived epitope. The chimeric antibodies embodied in the present invention include those that are derived from naturally occurring antibodies as well as chimeric antibodies made by means of genetic engineering technology well known to those of skill in the art.

The invention also provides methods for screening compounds for their ability to inhibit, facilitate or modulate the biochemical activity of the excitatory amino acid transporter molecules of the invention, for use in the in vitro screening of novel agonist and antagonist compounds. In preferred embodiments, cells, particularly amphibian oocytes transformed with a recombinant expression construct of the invention are contacted with such a compound, and the effect of the compound on the transport of the appropriate amino acid is assayed. Additional preferred embodiments comprise quantitative analyses of such effects. Also provided are assays that distinguish between the effect of such compounds on excitatory amino acid transport from effects of such compounds on chloride ion transport by the transporters of the invention.

As provided by the invention, such assays comprise a cell, most preferably a mammalian cell comprising a recombinant expression construct of the invention and expressing the excitatory amino acid transporter protein of the invention thereby, or an amphibian oocyte comprising a nucleic acid encoding an excitatory amino acid transporter protein of the invention and expressing said transporter thereby. In the practice of the methods of the invention, transporter activity is assayed using detectably-labeled excitatory amino acids or analogues thereof. In alternative embodiments, the electrophysiological and electrochemical effect of contacting such cells with an excitatory amino acid are assayed. Comparative assays performed in the presence or absence of putative analogues, agonists, antagonists, inhibitors, facilitators or modulators of transporter activity are provided by the invention.

The present invention is also useful for the detection of inhibitors, analogues, agonists or antagonists, heretofore known or unknown, of the excitatory amino acid transporters of the invention, either naturally occurring or embodied as a drug. In preferred embodiments, such inhibitors, analogues, agonists or antagonists may be detected in blood, saliva, semen, cerebrospinal fluid, plasma, lymph, or any other bodily fluid. In additional preferred embodiment, the invention provides methods for detecting and identifying inhibitors, analogues, agonist, or antagonists that preferentially affect either the amino acid uptake function or the chloride ion channel function of the amino acid transporters of the invention.

In the practice of these embodiments of the invention, such assays comprise a cell or cell membrane, most preferably a mammalian cell comprising a recombinant expression construct of the invention and expressing the excitatory amino acid transporter protein of the invention thereby, or an amphibian oocyte comprising a nucleic acid encoding an excitatory amino acid transporter protein of the invention and expressing said transporter thereby. In the practice of the methods of the invention, transporter binding and activity are assayed using detectably-labeled excitatory amino acids or analogues thereof. In particular, the capacity for a mammalian sample comprising a fluid to compete with or inhibit binding of detectably-labeled excitatory amino acids or analogues thereof is assayed to detect the presence of inhibiting, modulating or competing compounds in a biological sample. Additionally, such assays are directed towards the effect of a biological sample comprising a fluid on the electrophysiological and electrochemical activity of excitatory amino acid transporter in response to the addition of an excitatory amino acid transporter substrate. Comparative assays performed in the presence or absence of the biological sample or appropriate dilutions thereof are also provided by the invention.

The Examples which follow are illustrative of specific embodiments of the invention, and various uses thereof. They set forth for explanatory purposes only, and are not to be taken as limiting the invention.

EXAMPLE 1

Isolation of a Human Excitatory Amino Acid Transporter c DNA

Excitatory amino acid transporters EAAT1, EAAT2 and EAAT3 have been disclosed in co-owned and co-pending U.S. Ser. No. 08/140,729, filed Oct. 20, 1993, now U.S. Pat. No. 5,658,782, issued Aug. 10, 1997, which is incorporated by reference herein in its entirety. Excitatory amino acid transporter EAAT4 has been disclosed in co-owned and co-pending U.S. Ser. No. 08/663,808, filed Jun. 14, 1996, which is incorporated by reference herein in its entirety.

A novel human excitatory amino acid transporter was cloned from retinal tissues using well-established techniques (see Sambrook et al., 1990, *Molecular Cloning: A Laboratory Manual* (Cold Springs Harbor Press: New York). Briefly, cDNA was prepared from human retinal mRNA and screened under conditions of reduced stringency with a glutamate transporter cDNA obtained from salamander retina. Plaque filter lifts from a λgt10 library of human retinal cDNA were hybridized overnight at 55° C. in a solution of 0.5M dibasic sodium phosphate, pH 7.5, 7% sodium dodecyl sulfate (SDS), 1 mM ethylenediamine tetraacetic acid (EDTA) and salamander cDNA $^{32}$P-radiolabeled by random priming at $10^6$ cpm/mL. After hybridization, filters were washed at 55° C. on 2x standard saline phosphate/EDTA (SSPE, composed of 0.3M NaCl, 0.02M dibasic sodium phosphate, pH 7.4 and 2 mM EDTA) and 1% SDS. Eight positively-hybridizing clones were isolated, and insert cDNA from these clones was separated from the λgt10 cloning vector by restriction enzyme digestion with EcoRI, subcloned into the plasmid pBSKII (obtained from Stratagene, LaJolla, Calif.) and characterized. The nucleotide sequence of two of these clones was determined for both DNA strands using a polymerase chain reaction-based sequencing system (PRISM, Applied Biosystems, Foster City, Calif.) and an automated DNA sequencer (Applied Biosystems Model 373 Stretch DNA Sequencer, Applied Biosystems). Sequence data analysis was performed using MacVector analysis software (IBI, New Haven, Conn.).

A portion of the nucleotide sequence of one of these clones, termed EAAT5, is shown in FIGS. 1A through 1C (SEQ ID No.: 9). This clone was 2.9 kilobases (kb) in length and was found to comprise 180 basepairs (bp) of 5' untranslated sequence containing two in-frame translation stop codons upstream (5') from a consensus Kozak sequence providing a translation initiation codon (ACCATGG). The clone contains an open reading frame following this translation initiation codon of 1683 bp, followed by approximately 1.1 kb of 3' untranslated sequence, 326 bp of which is shown in FIG. 1C. Analysis of the other clone, which was about 3.1 kb in length, suggested that the retinal tissue mRNA corresponding to EAAT5 was about 3.1 kb in length.

The predicted gene product of EAAT5 is 560 amino acids in length (SEQ ID No.: 10) and has a predicted molecular weight (prior to any post-translational modifications) of about 61 kilodaltons. A comparison of the EAAT5 amino acid sequence with the other EAAT subtypes is shown in FIG. 2, and indicates that EAAT5 is a related but distinct member of the family of EAAT subtypes. For example, the EAAT5 sequence contains a single N-linked glycosylation site (NXS/T) in a putative large extracellular loop, while EAAT1, EAAT2 and EAAT3 through 3 contain 2 such sites and EAAT4 contains 3 of these sites. Using optimal sequence alignment, EAAT5 has 46% sequence identity with EAAT1, 43% sequence identity with EAAT4, 37% sequence identity with EAAT3 and 365% sequence identity with EAAT2. (For comparison, EAAT1 has 52% sequence identity with EAAT4 and 49% with EAAT3, as disclosed in U.S. Pat. No. 5,658,782 and U.S. Ser. No. 08/663,808). The most striking sequence conservation observed between these different subtypes is found in a large hydrophobic sequence that includes the sequence AAIFIAQ (residues 388–394 in EAAT5). However., both the amino and carboxyl termini of these proteins, which are believed to be topographically arranged intracellularly, are poorly conserved. Notably, the amino acid sequence of the carboxyl terminus of EAAT5 conform to a sequence motif found in synaptic membrane proteins: E-(S/T)-X-V-COOH (see Sheng, 1996, *Neuron* 17: 575–578for review). Table I provides a comparison of the EAAT5 carboxyl terminal amino acid sequence with those of the NMDA receptor subunits NR2A and NR2B and the Shaker-type potassium channel Kv1.4:

TABLE I

| Protein | C-terminal sequence |
|---|---|
| EAAT5 | S-E-L-E-T-N-V |
| NR2A | P-S-I-E-S-D-V |
| NR2B | S-S-I-E-S-D-V |
| Kv1.4 | K-A-V-E-T-D-V |

In these other proteins, interactions with a post-synaptic specific protein, postsynaptic density protein-95 (PSD-95), and particularly with certain domains of this protein (termed PDZ modular protein binding domains) have been studied, and the sequence similarity in EAAT5 indicates that EAAT5 should also interact with PSD-95. Preliminary results using a yeast two hybrid assay for protein-protein interactions indicate that EAAT5 has the ability to interact with PSD-95.

These results indicate that EAAT5 is a novel member of the excitatory amino acid transporter gene family that is expressed in retina.

EXAMPLE 2

Tissue Distribution of EAAT5 Expression

The tissue distribution of mRNA expression of the EAAT5 gene disclosed herein was determined in various tissues by Northern hybridization analysis (see Sambrook et al., ibid.) using human EAAT5 as a hybridization probe. The results of these experiments are shown in FIG. 3.

Human retinal poly(A)$^+$ RNA (2 $\mu$g) was size-fractionated by denaturing formaldehyde agarose gel electrophoresis and transferred to a nylon membrane (Sambrook et al., ibid.). This membrane and Multiple Tissue Northern Blot (Clonetech, Palo Alto, Calif.) were hybridized with human EAAT5 coding sequence that had been radiolabeled with $^{32}$P-dCTP (New England Nuclear, Boston, Mass.) by random priming (using a kit obtained from Boehringer Mannheim, Indianapolis, Ind.). Filters were hybridized overnight at 42° C. in a solution of 5× SSPE, 50% formamide, 7.5% Denhardt's solution, 2% SDS, 100 $\mu$g/mL denatured salmon sperm DNA and $10^6$ cpm/mL radiolabeled probe. Hybridization was visualized by autoradiography following two 30-min room temperature washes of the hybridized membranes in 2× SSPE/0.1% SDS followed by two 20-min washes at 50° C. in 0.1× SSPE/0.1% SDS. After autoradiography those membranes were stripped and re-hybridized with a radiolabeled β-actin probe to provide a control for RNA loading variations in each size-fractionated RNA sample.

These Northern blot analyses shown in FIG. 3 indicate that a 3.1 kb mRNA species encoding EAAT5 is abundantly expressed in human retina. A band of about the same size is also detected in liver, but at expression levels at least 20-fold lower than in retina. Weak hybridizing bands of about 2 kb in size were also detected in heart and muscle, and a very light band of approximately 4.5 kb was seen in brain RNA. It was not determined whether these differently sized bands reflect differential processing of the EAAT5 gene in these tissues or cross-hybridization of the EAAT5 probe with a closely related gene. However, these RNA sizes do not correspond to any of the other known EAAT subtypes. In order to determine whether the weak hybridization in brain RNA reflected a restricted distribution in certain brain regions, 20 $\mu$g of total RNA isolated from six different human brain regions (frontal and motor cortex, hippocampus, thalamus, basal ganglia, and cerebellum) were assayed by Northern hybridization as described above. No hybridization signal was detected in these experiments.

These results strongly suggest that EAAT5 expression is retina-specific.

EXAMPLE 3

Functional of Expression EAAT5 in Xenopus Oocytes

The sequence similarity between EAAT5 as disclosed herein and the previously-identified glutamate transporters EAAT1 through EAAT4 suggested that the EAAT5 protein was also an excitatory amino acid transporter. The biochemical and electrochemical activity of the EAAT5 protein was assayed in Xenopus oocytes following microinjection of in vitro synthesized EAAT5-encoding RNA.

Briefly, the coding sequence of the EAAT5 cDNA shown in FIGS. 1A through 1C (SEQ ID No.: 9) was isolated with unique flanking restriction endonuclease recognition sites using a polymerase chain reaction (PCR)-based technique. In this method, each of the complementary primers used for PCR amplification of the EAAT5 coding sequence contained a sequence encoding a unique restriction endonuclease recognition site. The sense primer contained a recognition site for restriction enzyme Asp718, and the antisense primer contained a recognition site for XbaI. The complete sequence of each PCR primer used for this amplification reaction are:

EAAT5sense primer:
CGCCGGTACCTCACCATGGTGCCGCAT (SEQ ID No.: 13);

EAAT5 antisense primer:
CGCCTCTAGAGGCTCAGACATTGGTCTC (SEQ ID No.: 14).

PCR amplification was performed for 25 cycles, each cycle comprising 30 seconds at 94° C. (denaturation), 30 seconds at 55° C. (annealing) and 2 minutes at 72° C. (extension) in 100 μL reaction mixture containing 1 μM each oligonucleotide primer, 10 ng plasmid template cDNA, 300 μM each deoxynucleotide, reaction buffer and Vent polymerase (New England Biolabs, Needham, Mass.). Following PCR amplification, the product of the reaction was purified using standard techniques (see Saiki et al., 1988, Science 239: 487–491) and the amplified DNA digested with Asp718 and XbaI. The digested amplified DNA was then subcloned into plasmid pOTV (see Airriza et al., ibid.) for preparing RNA for expression experiments in Xenopus oocytes.

EAAT5 RNA was prepared as follows. pOTV plasmid comprising the subcloned EAAT5 amplified cDNA as described was digested with restriction endonuclease SpeI and synthetic RNA transcribed using T7 RNA polymerase and a mMessage mMachine RNA capping kit (Ambion, Austin, Tex.). EAAT5 mRNA so prepared was then diluted with water to a concentration of 400 μg/mL, and 50 μnL of this EAAT5 mRNA was then microinjected into defolliculated stage V–VI Xenopus laevis oocytes. Oocytes were prepared as described (Quick & Lesier, 1994, Methods in Neuroscience 19: 261–279) and used for expression experiments 2–5 days later.

Radiolabeled glutamate uptake experiments were performed at room temperature under voltage clamp at −60 mV (except, where noted, at +10 mV). Currents were recorded during bath application of 100 μM ($^3$H)-L-glutamate (obtained from New England Nuclear, Boston, Mass.) in Ringers solution (96 mM NaCl, 2 mM KCl, 1.8 mM CaCl$_2$, 1 mM MgCl$_2$, and 5 mM HEPES, pH 7.5) for 100 seconds, the tritiated L-glutamate having a specific activity of 20 Ci/mmol. After 100 second incubation in the presence of tritiated substrate, oocytes were washed in the bath for 3 minutes to reduce background radioactivity, and then individually lysed for>15 minutes in a scintillation vial containing 1% SDS. After cell lysis, scintillation cocktail was added to each vial and the amount of radioactivity counted.

The results of these experiments are shown in FIG. 4A. Uptake of radiolabeled glutamate was significantly increased over uninjected oocytes (typically 2- to 10-fold); however, this was less of a difference when comparing the amount of radiolabeled glutamate uptake in cells expressing EAAT-1, -2 or -3 (which was typically 50-fold; see U.S. Pat. No. 5,658,782). EAAT5 glutamate uptake was found to be both sodium- and voltage dependent, as evidenced by comparison of the amount of radiolabeled glutamate uptake in the absence of sodium (by replacement of sodium ions by N-methyl glucamine, represented in the Figure as "0 Na$^+$") and by the difference in radiolabeled glutamate uptake in voltage clamped experiments performed at +10 mV (represented by "+10" in the Figure). EAAT5 was similar to all other known EAAT subtypes in that glutamate uptake was not significantly affected by replacing external chloride ion with gluconate.

Two electrode voltage clamp recordings from EAAT5 expressing oocytes were performed at room temperature using glass microelectrodes filled with 3M KCl solution (resistance<1MΩ) and a Ag/AgCl pellet bath ground or an active bath probe. An Axon GeneClamp 500 amplifier was used with Digidata 1200 interfaces and controlled using pClamp6 software (Axon Instruments, Foster City, Calif.). Steady state currents were filtered at 2 kHz and digitized at 5 kHz. For current-voltage curves, the oocyte membrane potential was held at −30 mV and stepped through a range of +50 to −100 in 100 millisecond steps. Steady state currents were measured during the final 20 milliseconds of the command step.

The results of these experiments are shown in FIG. 4B. Application of glutamate to oocytes expressing EAAT5 generated a current that was both voltage and concentration dependent. The current was found to reverse at −20±1 mV, and this reversal potential was not affected by the glutamate concentration. Although nor predicted for an EAAT transporter, a outward current was observed that was similar to the outward current observed in oocytes expressing the EAAT4 transporter (as disclosed in co-owned and co-pending U.S. Ser. No. 08/663,808). Currents were also elicited by L- and D-aspartate and, much less potently, by D-glutamate. The apparent affinity (EC$_{50}$) and maximum current (I$_{max}$) for these compounds at a membrane potential held at −60 mV is shown in Table II:

TABLE II

| Compound | n | EC$_{50}$, μM | I$_{max}$ |
|---|---|---|---|
| L-glutamate | 5 | 64 ± 6 | (1) |
| D-glutamate | 4 | >10,000 | (0.21 ± 0.06) |
| L-aspartate | 5 | 13 ± 5 | 0.67 ± 0.20 |
| D-aspartate | 4 | 64 ± 10 | 0.72 ± 0.03 |
| THA | 6 | 1.0 ± 0.1 | (0) |
| tPDC | 4 | 6.2 ± 1.7 | (0) | where I$_{max}$ is normalized to L-glutamate I$_{max}$ in the same oocyte. L-trans-pyrollidine-2,4-dicarboxylic acid (THA) and threo-β-hydroxyaspartate (tPDC) did not induce currents in th(se oocytes. EAAT5 exhibits considerable stereospecificity for L-glutamate over D-glutamate, and a slight preference for L-aspartate over D-aspartate, and the affirnty for L-glutamate is modestly voltage-dependent, increasing e-fold per 86 mV.

Both THA and tPDC were found to be potent blockers of both glutamate uptake (shown in FIG. 4A) and in the glutamate-elicited current in EAAT5-expressing oocytes. These results are shown in FIGS. 4C and 4D. Co-application of either 100 μM THA or 100 μM tPDC with glutamate almost entirely abolished the elicited current, as shown in these Figures. Neither compound generated a current with a voltage dependence similar to that of glutamate, even though these compounds acted as competitive substrates of other EAAT subtypes. In fact, both compounds applied to EAAT5-expressing oocytes alone elicited outward currents at negative potentials which became small and inward at positive potentials. In contrast, the high affinity EAAT2 subtype blocker kainate had minimal effect on EAAT5 function: in five cells tested, 1 mM kainate reduced the response to 100 μM glutamate to 84±11% of control over the range of −100 to −40 mV.

The dependence of EAAT5 glutamate-elicited currents on sodium and chloride ions is shown in FIGS. 5A through 5D. Sodium ion dependence is illustrated in FIG. 5A, where glutamate-elicited current is abolished in experiments performed in Ringer's solution in which sodium ions are replaced with N-methyl glucamine. These results reflect the sodium ion dependence observed for radiolabeled glutamate uptake shown in FIG. 4A. Replacing chloride ion with gluconate ion, on the other hand, had no effect on steady state glutamate induced inward current but was observed to eliminate the outward current (FIG. 5B). This result suggested that at least a portion of the glutamate-induced outward current was the result of passive flux of chloride ions, consistent with the behavior of other EAAT subtypes. To further characterize this chloride ion dependence, oocytes were dialyzed in chloride-free media for at least 48 hours prior to voltage clamp experiments performed in the absence of external chloride ion; the results of these assays are shown in FIG. 5C. Dialysis was found to abolish glutamate-elicited current in all ten cells tested, while control oocytes showed the normal steady state current induced by application of 100 μM glutamine to EAAT5-expressing oocytes. In additional experiments, external chloride ion was replaced by nitrate (FIG. 5D): in these experiments, nitrate substantially increased the glutamate-elicited outward current due to the influx of the more permeant nitrate ion as external anion. These results are consistent with the observed behavior of other EAAT subtypes in voltage clamp experiments performed in the presence of 100 μM glutamate and external nitrate ion.

These results demonstrated that the EAAT5 protein of the receptor exhibits biochemical and electrochemical properties of an excitatory amino acid transporter. These results are also consistent with EAAT5 being involved with a glutamate-gated chloride conductance associated with both presynaptic and postsynaptic aspects of the retinal light response. The human EAAT5 protein disclosed herein exhibits the ion-dependence and most of the pharmacological properties of retinal glutamate-related biochemical activities previously observed and unexplained in the art.

EXAMPLE 4

Construction of Fusion Proteins-Recombinant Expression Constructs for Expression of Immunologically-Active Epitopes of Amino Acid Transporters The EAAT5 amino acid transporter protein of the invention are expressed as fusion proteins in bacteria to produce immunologically-active epitopes. In these experiments, the amino acid transporters cDNAs of the invention are excised from their respective pOTV-containing constructs and subcloned into a pGEX-2T construct (Pharmacia, Piscataway, N.J.) whereby the coding sequences of the amino acid transporter cDNA is translationally in-frame with sequences encoding glutathione-S-transferase (described in Arriza et al., 1992, *J. Neurosci* 12: 4045–4055), termed pGST-EAAT5 constructs. After introduction of the pGST-EAAT5 constructs into bacterial cells (*E. coli*, strain D5α) using conventional techniques (see Sambrook et al., ibid), fusion protein expression is induced with isopropyl-1-thio-β-D-galactopyranoside as described (Smith & Johnson, 1988, *Gene* 67: 31–40) and purified using glutathione-Sepharose 4B (Pharmacia). Antilodies are then raised against the amino acid transporter of the invention by inoculation of rabbits with 300–500 μg of purified fusion protein in Freund's adjuvant (Grand Island Biological C., Grand Island, N.Y.), said inoculation repeated approximately every 4 weeks. Sera are immunoaffinit-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by imrmunoblotting using conventional techniques (Harlow & Lane, 1988, *Antihodies: A Laboratory Manual*, Cold Spring Harbor Laboratory Press, Cold Spring Harbor, N.Y.).

It should be understood that the foregoing disclosure emphasized certain specific embodiments of the invention and that all modification or alternatives equivalent thereto are within the spirit and scope of the invention as set forth in the appended claims.

---

What is claimed is:

1. A method of screening a compound for binding to an excitatory amino acid transporter in cells expressing the excitatory amino acid transporter, the method comprising the following steps:

(a) transforming a host cell with a recombinant expression construct encoding a human excitatory amino acid transporter EAAT5, wherein the cells of the transformed cell culture express the transporter; and (b) assaying the transformed cell with the compound to determine whether the compound binds to the excitatory amino acid transporter.

2. The method of claim 1, wherein the human excitatory amino acid transporter is human EAAT5 having an amino acid sequence identified as SEQ ID No. 10.

3. A method of screening a compound for competitive binding to an excitatory amino acid transporter in cells expressing the excitatory amino acid transporter, the method comprising the following steps:

(a) transforming a host cell with a recombinant expression construct encoding a human excitatory amino acid transporter EAAT5, wherein the cells of the transformed cell culture express the transporter; and (b) assaying the transformed cell with the compound in the presence and in the absence of an agonist for the excitatory amino acid transporter; and (c) determining whether the compound competes with the agonist for binding to the excitatory amino acid transporter.

4. The method of claim 3, wherein the human excitatory amino acid transporter is human EAAT5 having an amino acid sequence identified as SEQ ID No. 10.

5. The method of claim 3, wherein the compound is detectably-labeled.

6. The method of claim 3, wherein the excitatory amino acid transporter agonist is detectably-labeled.

7. The method of claim 3, wherein the excitatory amino acid transport competitor is quantitatively characterized by assaying the transformed cell culture with varying amounts of the competitor in the presence of a detectably-labeled excitatory amino acid or analogue thereof and measuring the extent of competition with excitatory amino acid transport thereby.

8. A method of screening a compound to determine if the compound is an inhibitor of an excitatory amino acid transporter in cells expressing the excitatory amino acid transporter, the method comprising the following steps:

(a) transforming a host cell with a recombinant expression construct encoding a human excitatory amino acid transporter EAAT5, wherein the cells of the transformed cell culture express the transporter; and (b) assaying the transformed cell culture with the compound to determine whether the compound is capable of inhibiting excitatory amino acid transport by the excitatory amino acid transporter.

9. The method of claim 8, wherein the human excitatory amino acid transporter is human EAAT5 having an amino acid sequence identified as SEQ ID No. 10.

10. The method of claim 8, wherein the excitatory amino acid transport inhibitor is quantitatively characterized by assaying the transformed cell culture with varying amounts of the inhibitor in the presence of a detectably-labeled excitatory amino acid or analogue thereof and measuring the extent of inhibition of excitatory amino acid transport thereby.

11. The method of claim 10, wherein the human excitatory amino acid transporter is human EAAT5 having an amino acid sequence identified as SEQ ID No. 10.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1680 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..1656

(xi) SEQUENCE DESCRIPTION: SEQ ID NO:1:

```
AAAGAAGAGA CCCTCCTAGA AAAGTAAAAT ATG ACT AAA AGC AAT GGA GAA GAG        54
                                Met Thr Lys Ser Asn Gly Glu Glu
                                  1               5

CCC AAG ATG GGG GGC AGG ATG GAG AGA TTC CAG CAG GGA GTC CGT AAA       102
```

-continued

```
Pro Lys Met Gly Gly Arg Met Glu Arg Phe Gln Gln Gly Val Arg Lys
     10                  15                  20

CGC ACA CTT TTG GCC AAG AAG AAA GTG CAG AAC ATT ACA AAG GAG GTT      150
Arg Thr Leu Leu Ala Lys Lys Lys Val Gln Asn Ile Thr Lys Glu Val
 25              30                  35                  40

GTT AAA AGT TAC CTG TTT CGG AAT GCT TTT GTG CTC CTC ACA GTC ACC      198
Val Lys Ser Tyr Leu Phe Arg Asn Ala Phe Val Leu Leu Thr Val Thr
                 45                  50                  55

GCT GTC ATT GTG GGT ACA ATC CTT GGA TTT ACC CTC CGA CCA TAC AGA      246
Ala Val Ile Val Gly Thr Ile Leu Gly Phe Thr Leu Arg Pro Tyr Arg
                     60                  65                  70

ATG AGC TAC CGG GAA GTC AAG TAC TTC TCC TTT CCT GGG GAA CTT CTG      294
Met Ser Tyr Arg Glu Val Lys Tyr Phe Ser Phe Pro Gly Glu Leu Leu
         75                  80                  85

ATG AGG ATG TTA CAG ATG CTG GTC TTA CCA CTT ATC ATC TCC AGT CTT      342
Met Arg Met Leu Gln Met Leu Val Leu Pro Leu Ile Ile Ser Ser Leu
         90                  95                 100

GTC ACA GGA ATG GCG GCG CTA GAT AGT AAG GCA TCA GGG AAG TGG GAA      390
Val Thr Gly Met Ala Ala Leu Asp Ser Lys Ala Ser Gly Lys Trp Glu
105                 110                 115                 120

TGC GGA GCT GTA GTC TAT TAT ATG ACT ACC ACC ATC ATT GCT GTG GTG      438
Cys Gly Ala Val Val Tyr Tyr Met Thr Thr Thr Ile Ile Ala Val Val
                125                 130                 135

ATT GGC ATA ATC ATT GTC ATC ATC ATC CAT CCT GGG AAG GGC ACA AAG      486
Ile Gly Ile Ile Ile Val Ile Ile Ile His Pro Gly Lys Gly Thr Lys
                140                 145                 150

GAA AAC ATG CAC AGA GAA GGC AAA ATT GTA CGA GTG ACA GCT GCA GAT      534
Glu Asn Met His Arg Glu Gly Lys Ile Val Arg Val Thr Ala Ala Asp
            155                 160                 165

GCC TTC CTG GAC TTG ATC AGG AAC ATG TTA AAT CCA AAT CTG GTA GAA      582
Ala Phe Leu Asp Leu Ile Arg Asn Met Leu Asn Pro Asn Leu Val Glu
        170                 175                 180

GCC TGC TTT AAA CAG TTT AAA ACC AAC TAT GAG AAG AGA AGC TTT AAA      630
Ala Cys Phe Lys Gln Phe Lys Thr Asn Tyr Glu Lys Arg Ser Phe Lys
185                 190                 195                 200

GTG CCC ATC CAG GCC AAC GAA ACG CTT GTG GGT GCT GTG ATA AAC AAT      678
Val Pro Ile Gln Ala Asn Glu Thr Leu Val Gly Ala Val Ile Asn Asn
                205                 210                 215

GTG TCT GAG GCC ATG GAG ACT CTT ACC CGA ATC ACA GAG GAG CTG GTC      726
Val Ser Glu Ala Met Glu Thr Leu Thr Arg Ile Thr Glu Glu Leu Val
            220                 225                 230

CCA GTT CCA GGA TCT GTG AAT GGA GTC AAT GCC CTG GGT CTA GTT GTC      774
Pro Val Pro Gly Ser Val Asn Gly Val Asn Ala Leu Gly Leu Val Val
        235                 240                 245

TTC TCC ATG TGC TTC GGT TTT GTG ATT GGA AAC ATG AAG GAA CAG GGG      822
Phe Ser Met Cys Phe Gly Phe Val Ile Gly Asn Met Lys Glu Gln Gly
    250                 255                 260

CAG GCC CTG AGA GAG TTC TTT GAT TCT CTT AAC GAA GCC ATC ATG AGA      870
Gln Ala Leu Arg Glu Phe Phe Asp Ser Leu Asn Glu Ala Ile Met Arg
265                 270                 275                 280

CTG GTA GCA GTA ATA ATG TGG TAT GCC CCC GTG GGT ATT CTC TTC CTG      918
Leu Val Ala Val Ile Met Trp Tyr Ala Pro Val Gly Ile Leu Phe Leu
                285                 290                 295

ATT GCT GGG AAG ATT GTG GAG ATG GAA GAC ATG GGT GTG ATT GGG GGG      966
Ile Ala Gly Lys Ile Val Glu Met Glu Asp Met Gly Val Ile Gly Gly
            300                 305                 310

CAG CTT GCC ATG TAC ACC GAG ACT GTC ATT GTT GGC TTA CTC ATT CAC     1014
Gln Leu Ala Met Tyr Thr Glu Thr Val Ile Val Gly Leu Leu Ile His
        315                 320                 325

GCA GTC ATC GTC TTG CCA CTC CTC TAC TTC TTG GTA ACA CGG AAA AAC     1062
```

```
Ala Val Ile Val Leu Pro Leu Leu Tyr Phe Leu Val Thr Arg Lys Asn
    330                     335                 340

CCT TGG GTT TTT ATT GGA GGG TTG CTG CAA GCA CTC ATC ACC GCT CTG    1110
Pro Trp Val Phe Ile Gly Gly Leu Leu Gln Ala Leu Ile Thr Ala Leu
345                     350                 355                 360

GGG ACC TCT TCA AGT TCT GCC ACC CTA CCC ATC ACC TTC AAG TGC CTG    1158
Gly Thr Ser Ser Ser Ser Ala Thr Leu Pro Ile Thr Phe Lys Cys Leu
                365                 370                 375

GAA GAG AAC AAT GGC GTG GAC AAG CGC GTC ACC AGA TTC GTG CTC CCC    1206
Glu Glu Asn Asn Gly Val Asp Lys Arg Val Thr Arg Phe Val Leu Pro
            380                 385                 390

GTA GGA GCC ACC ATT AAC CTG GAT GGG ACT GCC CTC TAT GAG GCT TTG    1254
Val Gly Ala Thr Ile Asn Leu Asp Gly Thr Ala Leu Tyr Glu Ala Leu
        395                 400                 405

GCT GCC ATT TTC ATT GCT CAA GTT AAC AAC TTT GAA CTG AAC TTC GGA    1302
Ala Ala Ile Phe Ile Ala Gln Val Asn Asn Phe Glu Leu Asn Phe Gly
    410                 415                 420

CAA ATT ATT ACA ATC AGC ATC ACA GCC ACA GCT GCC AGT ATT GGG GCA    1350
Gln Ile Ile Thr Ile Ser Ile Thr Ala Thr Ala Ala Ser Ile Gly Ala
425                 430                 435                 440

GCT GGA ATT CCT CAG GCG GGC CTG GTC ACT ATG GTC ATT GTG CTG ACA    1398
Ala Gly Ile Pro Gln Ala Gly Leu Val Thr Met Val Ile Val Leu Thr
                445                 450                 455

TCT GTC GGC CTG CCC ACT GAC GAC ATC ACG CTC ATC ATC GCG GTG GAC    1446
Ser Val Gly Leu Pro Thr Asp Asp Ile Thr Leu Ile Ile Ala Val Asp
            460                 465                 470

TGG TTC TTG GAT CGC CTC CGG ACC ACC ACC AAC GTA CTG GGA GAC TCC    1494
Trp Phe Leu Asp Arg Leu Arg Thr Thr Thr Asn Val Leu Gly Asp Ser
        475                 480                 485

CTG GGA GCT GGG ATT GTG GAG CAC TTG TCA CGA CAT GAA CTG AAG AAC    1542
Leu Gly Ala Gly Ile Val Glu His Leu Ser Arg His Glu Leu Lys Asn
    490                 495                 500

AGA GAT GTT GAA ATG GGT AAC TCA GTG ATT GAA GAG AAT GAA ATG AAG    1590
Arg Asp Val Glu Met Gly Asn Ser Val Ile Glu Glu Asn Glu Met Lys
505                 510                 515                 520

AAA CCA TAT CAA CTG ATT GCA CAG GAC AAT GAA ACT GAG AAA CCC ATC    1638
Lys Pro Tyr Gln Leu Ile Ala Gln Asp Asn Glu Thr Glu Lys Pro Ile
                525                 530                 535

GAC AGT GAA ACC AAG ATG TAGACTAACA TAAAGAAACA CTTT                  1680
Asp Ser Glu Thr Lys Met
                540
```

(2) INFORMATION FOR SEQ ID NO:2:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Lys Ser Asn Gly Glu Glu Pro Lys Met Gly Gly Arg Met Glu
1               5                   10                  15

Arg Phe Gln Gln Gly Val Arg Lys Arg Thr Leu Leu Ala Lys Lys Lys
                20                  25                  30

Val Gln Asn Ile Thr Lys Glu Val Val Lys Ser Tyr Leu Phe Arg Asn
            35                  40                  45

Ala Phe Val Leu Leu Thr Val Thr Ala Val Ile Val Gly Thr Ile Leu
        50                  55                  60

Gly Phe Thr Leu Arg Pro Tyr Arg Met Ser Tyr Arg Glu Val Lys Tyr
```

```
              65                   70                  75                  80
         Phe Ser Phe Pro Gly Glu Leu Leu Met Arg Met Leu Gln Met Leu Val
                         85                  90                  95
         Leu Pro Leu Ile Ile Ser Ser Leu Val Thr Gly Met Ala Ala Leu Asp
                         100                 105                 110
         Ser Lys Ala Ser Gly Lys Trp Glu Cys Gly Ala Val Val Tyr Tyr Met
                         115                 120                 125
         Thr Thr Thr Ile Ile Ala Val Val Ile Gly Ile Ile Val Ile Ile
                 130                 135                 140
         Ile His Pro Gly Lys Gly Thr Lys Glu Asn Met His Arg Glu Gly Lys
         145                 150                 155                 160
         Ile Val Arg Val Thr Ala Ala Asp Ala Phe Leu Asp Leu Ile Arg Asn
                         165                 170                 175
         Met Leu Asn Pro Asn Leu Val Glu Ala Cys Phe Lys Gln Phe Lys Thr
                         180                 185                 190
         Asn Tyr Glu Lys Arg Ser Phe Lys Val Pro Ile Gln Ala Asn Glu Thr
                         195                 200                 205
         Leu Val Gly Ala Val Ile Asn Asn Val Ser Glu Ala Met Glu Thr Leu
                         210                 215                 220
         Thr Arg Ile Thr Glu Glu Leu Val Pro Val Pro Gly Ser Val Asn Gly
         225                 230                 235                 240
         Val Asn Ala Leu Gly Leu Val Val Phe Ser Met Cys Phe Gly Phe Val
                         245                 250                 255
         Ile Gly Asn Met Lys Glu Gln Gly Gln Ala Leu Arg Glu Phe Phe Asp
                         260                 265                 270
         Ser Leu Asn Glu Ala Ile Met Arg Leu Val Ala Val Ile Met Trp Tyr
                         275                 280                 285
         Ala Pro Val Gly Ile Leu Phe Leu Ile Ala Gly Lys Ile Val Glu Met
                         290                 295                 300
         Glu Asp Met Gly Val Ile Gly Gly Gln Leu Ala Met Tyr Thr Glu Thr
         305                 310                 315                 320
         Val Ile Val Gly Leu Leu Ile His Ala Val Ile Val Leu Pro Leu Leu
                         325                 330                 335
         Tyr Phe Leu Val Thr Arg Lys Asn Pro Trp Val Phe Ile Gly Gly Leu
                         340                 345                 350
         Leu Gln Ala Leu Ile Thr Ala Leu Gly Thr Ser Ser Ser Ala Thr
                         355                 360                 365
         Leu Pro Ile Thr Phe Lys Cys Leu Glu Glu Asn Asn Gly Val Asp Lys
                         370                 375                 380
         Arg Val Thr Arg Phe Val Leu Pro Val Gly Ala Thr Ile Asn Leu Asp
         385                 390                 395                 400
         Gly Thr Ala Leu Tyr Glu Ala Leu Ala Ala Ile Phe Ile Ala Gln Val
                         405                 410                 415
         Asn Asn Phe Glu Leu Asn Phe Gly Gln Ile Ile Thr Ile Ser Ile Thr
                         420                 425                 430
         Ala Thr Ala Ala Ser Ile Gly Ala Ala Gly Ile Pro Gln Ala Gly Leu
                         435                 440                 445
         Val Thr Met Val Ile Val Leu Thr Ser Val Gly Leu Pro Thr Asp Asp
                         450                 455                 460
         Ile Thr Leu Ile Ile Ala Val Asp Trp Phe Leu Asp Arg Leu Arg Thr
         465                 470                 475                 480
         Thr Thr Asn Val Leu Gly Asp Ser Leu Gly Ala Gly Ile Val Glu His
                         485                 490                 495
```

```
Leu Ser Arg His Glu Leu Lys Asn Arg Asp Val Glu Met Gly Asn Ser
        500                 505                 510
Val Ile Glu Glu Asn Glu Met Lys Lys Pro Tyr Gln Leu Ile Ala Gln
        515                 520                 525
Asp Asn Glu Thr Glu Lys Pro Ile Asp Ser Glu Thr Lys Met
530                 535                 540
```

(2) INFORMATION FOR SEQ ID NO:3:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 34..1755

(xi) SEQUENCE DESCRIPTION: SEQ ID NO:3:

```
GATAGTGCTG AAGAGGAGGG GCGTTCCCAG ACC ATG GCA TCT ACG GAA GGT GCC       54
                                    Met Ala Ser Thr Glu Gly Ala
                                                        545

AAC AAT ATG CCC AAG CAG GTG GAA GTG CGA ATG CCA GAC AGT CAT CTT       102
Asn Asn Met Pro Lys Gln Val Glu Val Arg Met Pro Asp Ser His Leu
550                 555                 560                 565

GGC TCA GAG GAA CCC AAG CAC CGG CAC CTG GGC CTG CGC CTG TGT GAC       150
Gly Ser Glu Glu Pro Lys His Arg His Leu Gly Leu Arg Leu Cys Asp
                570                 575                 580

AAG CTG GGG AAG AAT CTG CTG CTC ACC CTG ACG GTG TTT GGT GTC ACT       198
Lys Leu Gly Lys Asn Leu Leu Leu Thr Leu Thr Val Phe Gly Val Thr
            585                 590                 595

CTG GGA GCA GTG TGT GGA GGG CTT CTT CGC TTG GCA TCT CCC ATC CAC       246
Leu Gly Ala Val Cys Gly Gly Leu Leu Arg Leu Ala Ser Pro Ile His
        600                 605                 610

CCT GAT GTG GTT ATG TTA ATA GCC TTC CCA GGG GAT ATA CTC ATG AGG       294
Pro Asp Val Val Met Leu Ile Ala Phe Pro Gly Asp Ile Leu Met Arg
    615                 620                 625

ATG CTA AAA ATG CTC ATT CTG GGT CTA ATC ATC TCC AGC TTA ATC ACA       342
Met Leu Lys Met Leu Ile Leu Gly Leu Ile Ile Ser Ser Leu Ile Thr
630                 635                 640                 645

GGG TTG TCA GGC CTG GAT GCT AAG GCT AGT GGC CGC TTG GGC ACG AGA       390
Gly Leu Ser Gly Leu Asp Ala Lys Ala Ser Gly Arg Leu Gly Thr Arg
                650                 655                 660

GCC ATG GTG TAT TAC ATG TCC ACG ACC ATC ATT GCT GCA GTA CTG GGG       438
Ala Met Val Tyr Tyr Met Ser Thr Thr Ile Ile Ala Ala Val Leu Gly
            665                 670                 675

GTC ATT CTG GTC TTG GCT ATC CAT CCA GGC AAT CCC AAG CTC AAG AAG       486
Val Ile Leu Val Leu Ala Ile His Pro Gly Asn Pro Lys Leu Lys Lys
        680                 685                 690

CAG CTC GGG CCT GGG AAG AAG AAT GAT GAA GTG TCC AGC CTG GAT GCC       534
Gln Leu Gly Pro Gly Lys Lys Asn Asp Glu Val Ser Ser Leu Asp Ala
    695                 700                 705

TTC CTG GAC CTT ATT CGA AAT CTC TTC CCT GAA AAC TTG GTC CAA GCC       582
Phe Leu Asp Leu Ile Arg Asn Leu Phe Pro Glu Asn Leu Val Gln Ala
710                 715                 720                 725

TGC TTT CAA CAG ATT CAA ACA GTG ACG AAG AAA GTC CTG GTT GCA CCA       630
Cys Phe Gln Gln Ile Gln Thr Val Thr Lys Lys Val Leu Val Ala Pro
                730                 735                 740

CCG CCA GAC GAG GAG GCC AAC GCA ACC AGC GCT GAA GTC TCT CTG TTG       678
Pro Pro Asp Glu Glu Ala Asn Ala Thr Ser Ala Glu Val Ser Leu Leu
```

-continued

|     | 745 | 750 | 755 |     |
|-----|-----|-----|-----|-----|

AAC GAG ACT GTG ACT GAG GTG CCG GAG GAG ACT AAG ATG GTT ATC AAG   726
Asn Glu Thr Val Thr Glu Val Pro Glu Glu Thr Lys Met Val Ile Lys
        760             765             770

AAG GGC CTG GAG TTC AAG GAT GGG ATG AAC GTC TTA GGT CTG ATA GGG   774
Lys Gly Leu Glu Phe Lys Asp Gly Met Asn Val Leu Gly Leu Ile Gly
775             780             785

TTT TTC ATT GCT TTT GGC ATC GCT ATG GGG AAG ATG GGA GAT CAG GCC   822
Phe Phe Ile Ala Phe Gly Ile Ala Met Gly Lys Met Gly Asp Gln Ala
790             795             800             805

AAG CTG ATG GTG GAT TTC TTC AAC ATT TTG AAT GAG ATT GTA ATG AAG   870
Lys Leu Met Val Asp Phe Phe Asn Ile Leu Asn Glu Ile Val Met Lys
            810             815             820

TTA GTG ATC ATG ATC ATG TGG TAC TCT CCC CTG GGT ATC GCC TGC CTG   918
Leu Val Ile Met Ile Met Trp Tyr Ser Pro Leu Gly Ile Ala Cys Leu
        825             830             835

ATC TGT GGA AAG ATC ATT GCA ATC AAG GAC TTA GAA GTG GTT GCT AGG   966
Ile Cys Gly Lys Ile Ile Ala Ile Lys Asp Leu Glu Val Val Ala Arg
        840             845             850

CAA CTG GGG ATG TAC ATG GTA ACA GTG ATC ATA GGC CTC ATC ATC CAC   1014
Gln Leu Gly Met Tyr Met Val Thr Val Ile Ile Gly Leu Ile Ile His
855             860             865

GGG GGC ATC TTT CTC CCC TTG ATT TAC TTT GTA GTG ACC AGG AAA AAC   1062
Gly Gly Ile Phe Leu Pro Leu Ile Tyr Phe Val Val Thr Arg Lys Asn
870             875             880             885

CCC TTC TCC CTT TTT GCT GGC ATT TTC CAA GCT TGG ATC ACT GCC CTG   1110
Pro Phe Ser Leu Phe Ala Gly Ile Phe Gln Ala Trp Ile Thr Ala Leu
            890             895             900

GGC ACC GCT TCC AGT GCT GGA ACT TTG CCT GTC ACC TTT CGT TGC CTG   1158
Gly Thr Ala Ser Ser Ala Gly Thr Leu Pro Val Thr Phe Arg Cys Leu
        905             910             915

GAA GAA AAT CTG GGG ATT GAT AAG CGT GTG ACT AGA TTC GTC CTT CCT   1206
Glu Glu Asn Leu Gly Ile Asp Lys Arg Val Thr Arg Phe Val Leu Pro
        920             925             930

GTT GGA GCA ACC ATT AAC ATG GAT GGT ACA GCC CTT TAT GAA GCG GTG   1254
Val Gly Ala Thr Ile Asn Met Asp Gly Thr Ala Leu Tyr Glu Ala Val
935             940             945

GCC GCC ATC TTT ATA GCC CAA ATG AAT GGT GTT GTC CTG GAT GGA GGA   1302
Ala Ala Ile Phe Ile Ala Gln Met Asn Gly Val Val Leu Asp Gly Gly
950             955             960             965

CAG ATT GTG ACT GTA AGC CTC ACA GCC ACC CTG GCA AGC GTC GGC GCG   1350
Gln Ile Val Thr Val Ser Leu Thr Ala Thr Leu Ala Ser Val Gly Ala
            970             975             980

GCC AGT ATC CCC AGT GCC GGG CTG GTC ACC ATG CTC CTC ATT CTG ACA   1398
Ala Ser Ile Pro Ser Ala Gly Leu Val Thr Met Leu Leu Ile Leu Thr
        985             990             995

GCC GTG GGC CTG CCA ACA GAG GAC ATC AGC TTG CTG GTG GCT GTG GAC   1446
Ala Val Gly Leu Pro Thr Glu Asp Ile Ser Leu Leu Val Ala Val Asp
        1000            1005            1010

TGG CTG CTG GAC AGG ATG AGA ACT TCA GTC AAT GTT GTG GGT GAC TCT   1494
Trp Leu Leu Asp Arg Met Arg Thr Ser Val Asn Val Val Gly Asp Ser
    1015            1020            1025

TTT GGG GCT GGG ATA GTC TAT CAC CTC TCC AAG TCT GAG CTG GAT ACC   1542
Phe Gly Ala Gly Ile Val Tyr His Leu Ser Lys Ser Glu Leu Asp Thr
1030            1035            1040            1045

ATT GAC TCC CAG CAT CGA GTG CAT GAA GAT ATT GAA ATG ACC AAG ACT   1590
Ile Asp Ser Gln His Arg Val His Glu Asp Ile Glu Met Thr Lys Thr
            1050            1055            1060

CAA TCC ATT TAT GAT GAC ATG AAG AAC CAC AGG GAA AGC AAC TCT AAT   1638
Gln Ser Ile Tyr Asp Asp Met Lys Asn His Arg Glu Ser Asn Ser Asn 5,989,825

31

32

-continued

```
                 1065                    1070                    1075
CAA TGT GTC TAT GCT GCA CAC AAC TCT GTC ATA GTA GAT GAA TGC AAG         1686
Gln Cys Val Tyr Ala Ala His Asn Ser Val Ile Val Asp Glu Cys Lys
            1080                    1085                    1090

GTA ACT CTG GCA GCC AAT GGA AAG TCA GCC GAC TGC AGT GTT GAG GAA         1734
Val Thr Leu Ala Ala Asn Gly Lys Ser Ala Asp Cys Ser Val Glu Glu
        1095                    1100                    1105

GAA CCT TGG AAA CGT GAG AAA TAAGGATATG AGTCTCAGCA AATTCTTGAA            1785
Glu Pro Trp Lys Arg Glu Lys
1110                    1115

TAAACTCCCC AGCGT                                                        1800
```

(2) INFORMATION FOR SEQ ID NO:4:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Thr Glu Gly Ala Asn Asn Met Pro Lys Gln Val Glu Val
1               5                   10                  15

Arg Met Pro Asp Ser His Leu Gly Ser Glu Pro Lys His Arg His
            20                  25                  30

Leu Gly Leu Arg Leu Cys Asp Lys Leu Gly Lys Asn Leu Leu Leu Thr
        35                  40                  45

Leu Thr Val Phe Gly Val Thr Leu Gly Ala Val Cys Gly Gly Leu Leu
    50                  55                  60

Arg Leu Ala Ser Pro Ile His Pro Asp Val Val Met Leu Ile Ala Phe
65                  70                  75                  80

Pro Gly Asp Ile Leu Met Arg Met Leu Lys Met Leu Ile Leu Gly Leu
                85                  90                  95

Ile Ile Ser Ser Leu Ile Thr Gly Leu Ser Gly Leu Asp Ala Lys Ala
            100                 105                 110

Ser Gly Arg Leu Gly Thr Arg Ala Met Val Tyr Tyr Met Ser Thr Thr
        115                 120                 125

Ile Ile Ala Ala Val Leu Gly Val Ile Leu Val Leu Ala Ile His Pro
    130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
            180                 185                 190

Lys Lys Val Leu Val Ala Pro Pro Asp Glu Ala Asn Ala Thr
        195                 200                 205

Ser Ala Glu Val Ser Leu Leu Asn Glu Thr Val Thr Glu Val Pro Glu
    210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255

Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
```

```
                      275                 280                 285
Pro Leu Gly Ile Ala Cys Leu Ile Cys Gly Lys Ile Ile Ala Ile Lys
    290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
                    325                 330                 335

Phe Val Val Thr Arg Lys Asn Pro Phe Ser Leu Phe Ala Gly Ile Phe
                340                 345                 350

Gln Ala Trp Ile Thr Ala Leu Gly Thr Ala Ser Ser Ala Gly Thr Leu
                355                 360                 365

Pro Val Thr Phe Arg Cys Leu Glu Glu Asn Leu Gly Ile Asp Lys Arg
370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
                    405                 410                 415

Gly Val Val Leu Asp Gly Gly Gln Ile Val Thr Val Ser Leu Thr Ala
                420                 425                 430

Thr Leu Ala Ser Val Gly Ala Ala Ser Ile Pro Ser Ala Gly Leu Val
                435                 440                 445

Thr Met Leu Leu Ile Leu Thr Ala Val Gly Leu Pro Thr Glu Asp Ile
450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
                    485                 490                 495

Ser Lys Ser Glu Leu Asp Thr Ile Asp Ser Gln His Arg Val His Glu
                500                 505                 510

Asp Ile Glu Met Thr Lys Thr Gln Ser Ile Tyr Asp Met Lys Asn
                515                 520                 525

His Arg Glu Ser Asn Ser Asn Gln Cys Val Tyr Ala Ala His Asn Ser
    530                 535                 540

Val Ile Val Asp Glu Cys Lys Val Thr Leu Ala Ala Asn Gly Lys Ser
545                 550                 555                 560

Ala Asp Cys Ser Val Glu Glu Pro Trp Lys Arg Glu Lys
                565                 570
```

(2) INFORMATION FOR SEQ ID NO:5:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 16..1590

(xi) SEQUENCE DESCRIPTION: SEQ ID NO:5:

```
ATAGCGGCGA CAGCC ATG GGG AAA CCG GCG AGG AAA GGA TGC CCG AGT TGG           51
              Met Gly Lys Pro Ala Arg Lys Gly Cys Pro Ser Trp
              575                 580                 585

AAG CGC TTC CTG AAG AAT AAC TGG GTG TTG CTG TCC ACC GTG GCC GCG           99
Lys Arg Phe Leu Lys Asn Asn Trp Val Leu Leu Ser Thr Val Ala Ala
        590                 595                 600
```

-continued

| | |
|---|---|
| GTG GTG CTA GGC ATT ACC ACA GGA GTC TTG GTT CGA GAA CAC AGC AAC<br>Val Val Leu Gly Ile Thr Thr Gly Val Leu Val Arg Glu His Ser Asn<br>           605                   610                615 | 147 |
| CTC TCA ACT CTA GAG AAA TTC TAC TTT GCT TTT CCT GGA GAA ATT CTA<br>Leu Ser Thr Leu Glu Lys Phe Tyr Phe Ala Phe Pro Gly Glu Ile Leu<br>    620                   625                 630 | 195 |
| ATG CGG ATG CTG AAA CTC ATC ATT TTG CCA TTA ATT ATA TCC AGC ATG<br>Met Arg Met Leu Lys Leu Ile Ile Leu Pro Leu Ile Ile Ser Ser Met<br>635                 640                 645              650 | 243 |
| ATT ACA GGT GTT GCT GCA CTG GAT TCC AAC GTA TCC GGA AAA ATT GGT<br>Ile Thr Gly Val Ala Ala Leu Asp Ser Asn Val Ser Gly Lys Ile Gly<br>           655                   660                665 | 291 |
| CTG CGC GCT GTC GTG TAT TAT TTC TGT ACC ACT CTC ATT GCT GTT ATT<br>Leu Arg Ala Val Val Tyr Tyr Phe Cys Thr Thr Leu Ile Ala Val Ile<br>             670                 675              680 | 339 |
| CTA GGT ATT GTG CTG GTG GTG AGC ATC AAG CCT GGT GTC ACC CAG AAA<br>Leu Gly Ile Val Leu Val Val Ser Ile Lys Pro Gly Val Thr Gln Lys<br>        685                   690                695 | 387 |
| GTG GGT GAA ATT GCG AGG ACA GGC AGC ACC CCT GAA GTC AGT ACG GTG<br>Val Gly Glu Ile Ala Arg Thr Gly Ser Thr Pro Glu Val Ser Thr Val<br>700                 705                   710 | 435 |
| GAT GCC ATG TTA GAT CTC ATC AGG AAT ATG TTC CCT GAG AAT CTT GTC<br>Asp Ala Met Leu Asp Leu Ile Arg Asn Met Phe Pro Glu Asn Leu Val<br>715                 720                 725             730 | 483 |
| CAG GCC TGT TTT CAG CAG TAC AAA ACT AAG CGT GAA GAA GTG AAG CCT<br>Gln Ala Cys Phe Gln Gln Tyr Lys Thr Lys Arg Glu Glu Val Lys Pro<br>             735                 740               745 | 531 |
| CCC AGC GAT CCA GAG ATG AAC ATG ACA GAA GAG TCC TTC ACA GCT GTC<br>Pro Ser Asp Pro Glu Met Asn Met Thr Glu Glu Ser Phe Thr Ala Val<br>           750                 755              760 | 579 |
| ATG ACA ACT GCA ATT TCC AAG AAC AAA ACA AAG GAA TAC AAA ATT GTT<br>Met Thr Thr Ala Ile Ser Lys Asn Lys Thr Lys Glu Tyr Lys Ile Val<br>765                 770                 775 | 627 |
| GGC ATG TAT TCA GAT GGC ATA AAC GTC CTG GGC TTG ATT GTC TTT TGC<br>Gly Met Tyr Ser Asp Gly Ile Asn Val Leu Gly Leu Ile Val Phe Cys<br>        780                   785              790 | 675 |
| CTT GTC TTT GGA CTT GTC ATT GGA AAA ATG GGA GAA AAG GGA CAA ATT<br>Leu Val Phe Gly Leu Val Ile Gly Lys Met Gly Glu Lys Gly Gln Ile<br>795                 800                 805             810 | 723 |
| CTG GTG GAT TTC TTC AAT GCT TTG AGT GAT GCA ACC ATG AAA ATC GTT<br>Leu Val Asp Phe Phe Asn Ala Leu Ser Asp Ala Thr Met Lys Ile Val<br>             815                 820              825 | 771 |
| CAG ATC ATC ATG TGT TAT ATG CCA CTA GGT ATT TTG TTC CTG ATT GCT<br>Gln Ile Ile Met Cys Tyr Met Pro Leu Gly Ile Leu Phe Leu Ile Ala<br>           830                 835              840 | 819 |
| GGG AAG ATC ATA GAA GTT GAA GAC TGG GAA ATA TTC CGC AAG CTG GGC<br>Gly Lys Ile Ile Glu Val Glu Asp Trp Glu Ile Phe Arg Lys Leu Gly<br>        845                 850              855 | 867 |
| CTT TAC ATG GCC ACA GTC CTG ACT GGG CTT GCA ATC CAC TCC ATT GTA<br>Leu Tyr Met Ala Thr Val Leu Thr Gly Leu Ala Ile His Ser Ile Val<br>860                 865                 870 | 915 |
| ATT CTC CCG CTG ATA TAT TTC ATA GTC GTA CGA AAG AAC CCT TTC CGA<br>Ile Leu Pro Leu Ile Tyr Phe Ile Val Val Arg Lys Asn Pro Phe Arg<br>875                 880                 885             890 | 963 |
| TTT GCC ATG GGA ATG GCC CAG GCT CTC CTG ACA GCT CTC ATG ATC TCT<br>Phe Ala Met Gly Met Ala Gln Ala Leu Leu Thr Ala Leu Met Ile Ser<br>           895                 900              905 | 1011 |
| TCC AGT TCA GCA ACA CTG CCT GTC ACC TTC CGC TGT GCT GAA GAA AAT<br>Ser Ser Ser Ala Thr Leu Pro Val Thr Phe Arg Cys Ala Glu Glu Asn<br>           910                 915              920 | 1059 |

```
AAC CAG GTG GAC AAG AGG ATC ACT CGA TTC GTG TTA CCC GTT GGT GCA        1107
Asn Gln Val Asp Lys Arg Ile Thr Arg Phe Val Leu Pro Val Gly Ala
            925                 930                 935

ACA ATC AAC ATG GAT GGG ACC GCG CTC TAT GAA GCA GTG GCA GCG GTG        1155
Thr Ile Asn Met Asp Gly Thr Ala Leu Tyr Glu Ala Val Ala Ala Val
940                 945                 950

TTT ATT GCA CAG TTG AAT GAC CTG GAC TTG GGC ATT GGG CAG ATC ATC        1203
Phe Ile Ala Gln Leu Asn Asp Leu Asp Leu Gly Ile Gly Gln Ile Ile
955                 960                 965                 970

ACC ATC AGT ATC ACG GCC ACA TCT GCC AGC ATC GGA GCT GCT GGC GTG        1251
Thr Ile Ser Ile Thr Ala Thr Ser Ala Ser Ile Gly Ala Ala Gly Val
            975                 980                 985

CCC CAG GCT GGC CTG GTG ACC ATG GTG ATT GTG CTG AGT GCC GTG GGC        1299
Pro Gln Ala Gly Leu Val Thr Met Val Ile Val Leu Ser Ala Val Gly
        990                 995                 1000

CTG CCC GCC GAG GAT GTC ACC CTG ATC ATT GCT GTC GAC TGG CTC TCG        1347
Leu Pro Ala Glu Asp Val Thr Leu Ile Ile Ala Val Asp Trp Leu Ser
            1005                1010                1015

GAC CGG TTC AGG ACC ATG GTC AAC GTC CTT GGT GAT GCT TTT GGG ACG        1395
Asp Arg Phe Arg Thr Met Val Asn Val Leu Gly Asp Ala Phe Gly Thr
1020                1025                1030

GGC ATT GTG GAA AAG CTC TCC AAG AAG GAG CTG GAG CAG ATG GAT GTT        1443
Gly Ile Val Glu Lys Leu Ser Lys Lys Glu Leu Glu Gln Met Asp Val
1035                1040                1045                1050

TCA TCT GAA GTC AAC ATT GTG AAT CCC TTT GCC TTG GAA TCC ACA ATC        1491
Ser Ser Glu Val Asn Ile Val Asn Pro Phe Ala Leu Glu Ser Thr Ile
            1055                1060                1065

CTT GAC AAC GAA GAC TCA GAC ACC AAG AAG TCT TAT GTC AAT GGA GGC        1539
Leu Asp Asn Glu Asp Ser Asp Thr Lys Lys Ser Tyr Val Asn Gly Gly
            1070                1075                1080

TTT GCA GTA GAC AAG TCT GAC ACC ATC TCA TTC ACC CAG ACC TCA CAG        1587
Phe Ala Val Asp Lys Ser Asp Thr Ile Ser Phe Thr Gln Thr Ser Gln
            1085                1090                1095

TTC TAGGGCCCCT GGCTGCAGAT GACTGGAAAC AAGGAAGGAC ATTTCGTGAG             1640
Phe

AGTCATCTCA AACACGGCTT AAGGAAAAGA GAAA                                  1674
```

(2) INFORMATION FOR SEQ ID NO:6:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Lys Pro Ala Arg Lys Gly Cys Pro Ser Trp Lys Arg Phe Leu
1               5                   10                  15

Lys Asn Asn Trp Val Leu Leu Ser Thr Val Ala Ala Val Val Leu Gly
                20                  25                  30

Ile Thr Thr Gly Val Leu Val Arg Glu His Ser Asn Leu Ser Thr Leu
            35                  40                  45

Glu Lys Phe Tyr Phe Ala Phe Pro Gly Glu Ile Leu Met Arg Met Leu
        50                  55                  60

Lys Leu Ile Ile Leu Pro Leu Ile Ile Ser Ser Met Ile Thr Gly Val
65                  70                  75                  80

Ala Ala Leu Asp Ser Asn Val Ser Gly Lys Ile Gly Leu Arg Ala Val
                85                  90                  95
```

```
Val Tyr Tyr Phe Cys Thr Thr Leu Ile Ala Val Ile Leu Gly Ile Val
            100                 105                 110

Leu Val Val Ser Ile Lys Pro Gly Val Thr Gln Lys Val Gly Glu Ile
            115                 120                 125

Ala Arg Thr Gly Ser Thr Pro Glu Val Ser Thr Val Asp Ala Met Leu
130                 135                 140

Asp Leu Ile Arg Asn Met Phe Pro Glu Asn Leu Val Gln Ala Cys Phe
145                 150                 155                 160

Gln Gln Tyr Lys Thr Lys Arg Glu Glu Val Lys Pro Pro Ser Asp Pro
                165                 170                 175

Glu Met Asn Met Thr Glu Glu Ser Phe Thr Ala Val Met Thr Thr Ala
            180                 185                 190

Ile Ser Lys Asn Lys Thr Lys Glu Tyr Lys Ile Val Gly Met Tyr Ser
            195                 200                 205

Asp Gly Ile Asn Val Leu Gly Leu Ile Val Phe Cys Leu Val Phe Gly
            210                 215                 220

Leu Val Ile Gly Lys Met Gly Glu Lys Gly Gln Ile Leu Val Asp Phe
225                 230                 235                 240

Phe Asn Ala Leu Ser Asp Ala Thr Met Lys Ile Val Gln Ile Ile Met
                245                 250                 255

Cys Tyr Met Pro Leu Gly Ile Leu Phe Leu Ile Ala Gly Lys Ile Ile
            260                 265                 270

Glu Val Glu Asp Trp Glu Ile Phe Arg Lys Leu Gly Leu Tyr Met Ala
            275                 280                 285

Thr Val Leu Thr Gly Leu Ala Ile His Ser Ile Val Ile Leu Pro Leu
            290                 295                 300

Ile Tyr Phe Ile Val Val Arg Lys Asn Pro Phe Arg Phe Ala Met Gly
305                 310                 315                 320

Met Ala Gln Ala Leu Leu Thr Ala Leu Met Ile Ser Ser Ser Ala
                325                 330                 335

Thr Leu Pro Val Thr Phe Arg Cys Ala Glu Glu Asn Asn Gln Val Asp
            340                 345                 350

Lys Arg Ile Thr Arg Phe Val Leu Pro Val Gly Ala Thr Ile Asn Met
            355                 360                 365

Asp Gly Thr Ala Leu Tyr Glu Ala Val Ala Ala Val Phe Ile Ala Gln
370                 375                 380

Leu Asn Asp Leu Asp Leu Gly Ile Gly Gln Ile Ile Thr Ile Ser Ile
385                 390                 395                 400

Thr Ala Thr Ser Ala Ser Ile Gly Ala Ala Gly Val Pro Gln Ala Gly
                405                 410                 415

Leu Val Thr Met Val Ile Val Leu Ser Ala Val Gly Leu Pro Ala Glu
            420                 425                 430

Asp Val Thr Leu Ile Ile Ala Val Asp Trp Leu Ser Asp Arg Phe Arg
            435                 440                 445

Thr Met Val Asn Val Leu Gly Asp Ala Phe Gly Thr Gly Ile Val Glu
            450                 455                 460

Lys Leu Ser Lys Lys Glu Leu Glu Gln Met Asp Val Ser Ser Glu Val
465                 470                 475                 480

Asn Ile Val Asn Pro Phe Ala Leu Glu Ser Thr Ile Leu Asp Asn Glu
            485                 490                 495

Asp Ser Asp Thr Lys Lys Ser Tyr Val Asn Gly Gly Phe Ala Val Asp
            500                 505                 510

Lys Ser Asp Thr Ile Ser Phe Thr Gln Thr Ser Gln Phe
            515                 520                 525
```

(2) INFORMATION FOR SEQ ID NO:7:

(i) SEQUENCE CHARACTERISTICS:
        (A) LENGTH: 1734 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 9..1700

(xi) SEQUENCE DESCRIPTION: SEQ ID NO:7:

```
GATAGACC ATG AGC AGC CAT GGC AAC AGC CTG TTC CTT CGG GAG AGC GGC         50
         Met Ser Ser His Gly Asn Ser Leu Phe Leu Arg Glu Ser Gly
           1               5                  10

CAG CGG CTG GGC CGG GTG GGC TGG CTG CAG CGG CTG CAG GAA AGC CTG          98
Gln Arg Leu Gly Arg Val Gly Trp Leu Gln Arg Leu Gln Glu Ser Leu
 15                  20                  25                  30

CAG CAG AGA GCA CTG CGC ACG CGC CTG CGC CTG CAG ACC ATG ACC CTC         146
Gln Gln Arg Ala Leu Arg Thr Arg Leu Arg Leu Gln Thr Met Thr Leu
                 35                  40                  45

GAG CAC GTG CTG CGC TTC CTG CGC CGA AAC GCC TTC ATT CTG CTG ACG         194
Glu His Val Leu Arg Phe Leu Arg Arg Asn Ala Phe Ile Leu Leu Thr
                     50                  55                  60

GTC AGC GCC GTG GTC ATT GGG GTC AGC CTG GCC TTT GCC CTG CGC CCA         242
Val Ser Ala Val Val Ile Gly Val Ser Leu Ala Phe Ala Leu Arg Pro
 65                  70                  75

TAT CAG CTC ACC TAC CGC CAG ATC AAG TAC TTC TCT TTT CCT GGA GAG         290
Tyr Gln Leu Thr Tyr Arg Gln Ile Lys Tyr Phe Ser Phe Pro Gly Glu
             80                  85                  90

CTT CTG ATG AGG ATG CTG CAG ATG CTG GTG TTA CCT CTC ATT GTC TCC         338
Leu Leu Met Arg Met Leu Gln Met Leu Val Leu Pro Leu Ile Val Ser
 95                 100                 105                 110

AGC CTG GTC ACA GGT ATG GCA TCC CTG GAC AAC AAG GCC ACG GGG CGG         386
Ser Leu Val Thr Gly Met Ala Ser Leu Asp Asn Lys Ala Thr Gly Arg
                115                 120                 125

ATG GGG ATG CGG GCA GCT GTG TAC TAC CTG GTG ACC ACC ATC ATC GCG         434
Met Gly Met Arg Ala Ala Val Tyr Tyr Leu Val Thr Thr Ile Ile Ala
                130                 135                 140

GTC TTC ATC GGC ATC CTC ATG GTC ACC ATC ATC CAT CCC GGG AAG GGC         482
Val Phe Ile Gly Ile Leu Met Val Thr Ile Ile His Pro Gly Lys Gly
145                 150                 155

TCC AAG GAG GGG CTG CAC CGG GAG GGC CGG ATC GAG ACC ATC CCC ACA         530
Ser Lys Glu Gly Leu His Arg Glu Gly Arg Ile Glu Thr Ile Pro Thr
160                 165                 170

GCT GAT GCC TTC ATG GAC CTG ATC AGA AAT ATG TTT CCA CCA AAC CTT         578
Ala Asp Ala Phe Met Asp Leu Ile Arg Asn Met Phe Pro Pro Asn Leu
175                 180                 185                 190

GTG GAG GCC TGC TTC AAA CAG TTG AAG ACG CAG TAC AGC ACG AGG GTG         626
Val Glu Ala Cys Phe Lys Gln Leu Lys Thr Gln Tyr Ser Thr Arg Val
                195                 200                 205

GTA ACC AGG ACC ATG GTG AGG ACA GAG AAC GGG TCT GAG CCG GTG GCC         674
Val Thr Arg Thr Met Val Arg Thr Glu Asn Gly Ser Glu Pro Val Ala
                210                 215                 220

TCC ATG CCT CCT CCA TTC TCA GTG GAG AAC GGA ACC AGC TTC CTG GAA         722
Ser Met Pro Pro Pro Phe Ser Val Glu Asn Gly Thr Ser Phe Leu Glu
                225                 230                 235

AAT GTC ACT CGG GCC TTG GGT ACC CTG CAG GAG ATG CTG AGC TTT GAG         770
Asn Val Thr Arg Ala Leu Gly Thr Leu Gln Glu Met Leu Ser Phe Glu
```

-continued

```
                 240                      245                     250
GAG ACT GTA CCC GTG CCT GGC TCC GCC AAT GGC ATC AAC GCC CTG GGC         818
Glu Thr Val Pro Val Pro Gly Ser Ala Asn Gly Ile Asn Ala Leu Gly
255                     260                     265                 270

CTC GTG GTC TTC TCT GTG GCC TTT GGG CTG GTC ATT GGT GGC ATG AAA         866
Leu Val Val Phe Ser Val Ala Phe Gly Leu Val Ile Gly Gly Met Lys
                275                     280                     285

CAC AAG GGC AGA GTC CTC AGG GAC TTC TTC GAC AGC CTC AAT GAG GCT         914
His Lys Gly Arg Val Leu Arg Asp Phe Phe Asp Ser Leu Asn Glu Ala
                    290                     295                 300

ATT ATG AGG CTG GTG GGC ATC ATT ATC TGG TAT GCA CCT GTG GGC ATC         962
Ile Met Arg Leu Val Gly Ile Ile Ile Trp Tyr Ala Pro Val Gly Ile
                305                     310                     315

CTG TTC CTG ATT GCT GGG AAG ATT CTG GAG ATG GAA GAC ATG GCC GTC        1010
Leu Phe Leu Ile Ala Gly Lys Ile Leu Glu Met Glu Asp Met Ala Val
320                     325                     330

CTG GGG GGT CAG CTG GGC ATG TAC ACC CTG ACC GTC ATC GTG GGC CTG        1058
Leu Gly Gly Gln Leu Gly Met Tyr Thr Leu Thr Val Ile Val Gly Leu
335                     340                     345                 350

TTC CTC CAT GCC GGC ATT GTC CTT CCC CTC ATC TAC TTC CTC GTC ACT        1106
Phe Leu His Ala Gly Ile Val Leu Pro Leu Ile Tyr Phe Leu Val Thr
                355                     360                     365

CAC CGG AAC CCC TTC CCC TTC ATT GGG GGC ATG CTA CAA GCC CTC ATC        1154
His Arg Asn Pro Phe Pro Phe Ile Gly Gly Met Leu Gln Ala Leu Ile
                370                     375                     380

ACC GCT ATG GGA ACG TCT TCC AGC TCG GCA ACG CTG CCC ATC ACC TTC        1202
Thr Ala Met Gly Thr Ser Ser Ser Ala Thr Leu Pro Ile Thr Phe
                385                     390                     395

CGC TGC CTG GAG GAG GGC CTG GGT GTG GAC CGC CGC ATC ACC AGG TTC        1250
Arg Cys Leu Glu Glu Gly Leu Gly Val Asp Arg Arg Ile Thr Arg Phe
400                     405                     410

GTC CTG CCC GTG GGC GCC ACG GTC AAC ATG GAT GGC ACT GCC CTC TAC        1298
Val Leu Pro Val Gly Ala Thr Val Asn Met Asp Gly Thr Ala Leu Tyr
415                     420                     425                 430

GAG GCC CTG GCT GCC ATC TTC ATT GCT CAA GTT AAC AAC TAC GAG CTC        1346
Glu Ala Leu Ala Ala Ile Phe Ile Ala Gln Val Asn Asn Tyr Glu Leu
                435                     440                     445

AAC CTG GGT CAG ATC ACA ACC ATC AGC ATC ACG GCC ACA GCA GCC AGT        1394
Asn Leu Gly Gln Ile Thr Thr Ile Ser Ile Thr Ala Thr Ala Ala Ser
                450                     455                     460

GTT GGG GCT GCT GGC ATC CCC CAG GCG GGT CTG GTC ACC ATG GTC ATT        1442
Val Gly Ala Ala Gly Ile Pro Gln Ala Gly Leu Val Thr Met Val Ile
                465                     470                     475

GTG CTT ACG TCG GTC GGC TTG CCC ACG GAA GAC ATC ACG CTC ATC ATC        1490
Val Leu Thr Ser Val Gly Leu Pro Thr Glu Asp Ile Thr Leu Ile Ile
480                     485                     490

GCC GTG GAC TGG TTC CTT GAC CGG CTT CGC ACA ATG ACC AAC GTA CTG        1538
Ala Val Asp Trp Phe Leu Asp Arg Leu Arg Thr Met Thr Asn Val Leu
495                     500                     505                 510

GGC CAC TCA ATT GGA GCG GCC GTC ATC GAG CAC TTG TCT CAG CGG GAG        1586
Gly His Ser Ile Gly Ala Ala Val Ile Glu His Leu Ser Gln Arg Glu
                515                     520                     525

CTG GAG CTT CAG GAA GCT GAG CTT ACC CTC CCC AGC CTG GGG AAA CCC        1634
Leu Glu Leu Gln Glu Ala Glu Leu Thr Leu Pro Ser Leu Gly Lys Pro
                530                     535                     540

TAC AAG TCC CTC ATG GCA CAG GAG AAG GGG GCA TCC CGG GGA CGG GGA        1682
Tyr Lys Ser Leu Met Ala Gln Glu Lys Gly Ala Ser Arg Gly Arg Gly
                545                     550                     555

GGC AAC GAG AGT GCT ATG TGAGGGGCCT CCAGCTCTGC CCCCCCAGAG AGGA          1734
Gly Asn Glu Ser Ala Met
```

560

(2) INFORMATION FOR SEQ ID NO:8:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Ser His Gly Asn Ser Leu Phe Leu Arg Glu Ser Gly Gln Arg
 1               5                  10                  15

Leu Gly Arg Val Gly Trp Leu Gln Arg Leu Gln Glu Ser Leu Gln Gln
             20                  25                  30

Arg Ala Leu Arg Thr Arg Leu Arg Leu Gln Thr Met Thr Leu Glu His
         35                  40                  45

Val Leu Arg Phe Leu Arg Arg Asn Ala Phe Ile Leu Leu Thr Val Ser
     50                  55                  60

Ala Val Val Ile Gly Val Ser Leu Ala Phe Ala Leu Arg Pro Tyr Gln
 65                  70                  75                  80

Leu Thr Tyr Arg Gln Ile Lys Tyr Phe Ser Phe Pro Gly Glu Leu Leu
                 85                  90                  95

Met Arg Met Leu Gln Met Leu Val Leu Pro Leu Ile Val Ser Ser Leu
            100                 105                 110

Val Thr Gly Met Ala Ser Leu Asp Asn Lys Ala Thr Gly Arg Met Gly
        115                 120                 125

Met Arg Ala Ala Val Tyr Tyr Leu Val Thr Thr Ile Ile Ala Val Phe
    130                 135                 140

Ile Gly Ile Leu Met Val Thr Ile Ile His Pro Gly Lys Gly Ser Lys
145                 150                 155                 160

Glu Gly Leu His Arg Glu Gly Arg Ile Glu Thr Ile Pro Thr Ala Asp
                165                 170                 175

Ala Phe Met Asp Leu Ile Arg Asn Met Phe Pro Pro Asn Leu Val Glu
            180                 185                 190

Ala Cys Phe Lys Gln Leu Lys Thr Gln Tyr Ser Thr Arg Val Val Thr
        195                 200                 205

Arg Thr Met Val Arg Thr Glu Asn Gly Ser Glu Pro Gly Ala Ser Met
    210                 215                 220

Pro Pro Pro Phe Ser Val Glu Asn Gly Thr Ser Phe Leu Glu Asn Val
225                 230                 235                 240

Thr Arg Ala Leu Gly Thr Leu Gln Glu Met Leu Ser Phe Glu Glu Thr
                245                 250                 255

Val Pro Val Pro Gly Ser Ala Asn Gly Ile Asn Ala Leu Gly Leu Val
            260                 265                 270

Val Phe Ser Val Ala Phe Gly Leu Val Ile Gly Gly Met Lys His Lys
        275                 280                 285

Gly Arg Val Leu Arg Asp Phe Phe Asp Ser Leu Asn Glu Ala Ile Met
    290                 295                 300

Arg Leu Val Gly Ile Ile Ile Trp Tyr Ala Pro Val Gly Ile Leu Phe
305                 310                 315                 320

Leu Ile Ala Gly Lys Ile Leu Glu Met Glu Asp Met Ala Val Leu Gly
                325                 330                 335

Gly Gln Leu Gly Met Tyr Thr Leu Thr Val Ile Val Gly Leu Phe Leu
            340                 345                 350
```

```
His Ala Gly Ile Val Leu Pro Leu Ile Tyr Phe Leu Val Thr His Arg
    355                 360                 365

Asn Pro Phe Pro Phe Ile Gly Met Leu Gln Ala Leu Ile Thr Ala
370                 375                 380

Met Gly Thr Ser Ser Ser Ala Thr Leu Pro Ile Thr Phe Arg Cys
385                 390                 395                 400

Leu Glu Glu Gly Leu Gly Val Asp Arg Arg Ile Thr Arg Phe Val Leu
                405                 410                 415

Pro Val Gly Ala Thr Val Asn Met Asp Gly Thr Ala Leu Tyr Glu Ala
                420                 425                 430

Leu Ala Ala Ile Phe Ile Ala Gln Val Asn Asn Tyr Glu Leu Asn Leu
            435                 440                 445

Gly Gln Ile Thr Thr Ile Ser Ile Thr Ala Thr Ala Ala Ser Val Gly
            450                 455                 460

Ala Ala Gly Ile Pro Gln Ala Gly Leu Val Thr Met Val Ile Val Leu
465                 470                 475                 480

Thr Ser Val Gly Leu Pro Thr Glu Asp Ile Thr Leu Ile Ile Ala Val
                485                 490                 495

Asp Trp Phe Leu Asp Arg Leu Arg Thr Met Thr Asn Val Leu Gly His
                500                 505                 510

Ser Ile Gly Ala Ala Val Ile Glu His Leu Ser Gln Arg Glu Leu Glu
            515                 520                 525

Leu Gln Glu Ala Glu Leu Thr Leu Pro Ser Leu Gly Lys Pro Tyr Lys
530                 535                 540

Ser Leu Met Ala Gln Glu Lys Gly Ala Ser Arg Gly Arg Gly Gly Asn
545                 550                 555                 560

Glu Ser Ala Met
```

(2) INFORMATION FOR SEQ ID NO:9:

(i) SEQUENCE CHARACTERISTICS:
        (A) LENGTH: 2194 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 189..1868

(xi) SEQUENCE DESCRIPTION: SEQ ID NO:9:

```
GAATTCCCCG TGTGGCCGCC TTAGAGGGAA GCCACACGGG CATGGCCGTG GGGCTGGCGA        60

CTGGTGTTTA GCAATCCCGA CCACCTGCCT GCTGAGGGGC TAGAGCCCTC AGCCCAGACC       120

CTGTGCCCCC GGCCGGGCTC TCATGCGTGG AATGGTGCTG TGCCCCTTGC CAGCAGGCCA       180

GGCTCACC ATG GTG CCG CAT ACC ATC TTG GCA CGG GGG AGG GAC GTG TGC        230
         Met Val Pro His Thr Ile Leu Ala Arg Gly Arg Asp Val Cys
             565                 570                 575

AGG CGG AAT GGA CTC CTC ATC CTG TCT GTG CTG TCT GTC ATC GTG GGC         278
Arg Arg Asn Gly Leu Leu Ile Leu Ser Val Leu Ser Val Ile Val Gly
580                 585                 590

TGC CTC CTC GGC TTC TTC TTG AGG ACC CGG CGC CTC TCA CCA CAG GAA         326
Cys Leu Leu Gly Phe Phe Leu Arg Thr Arg Arg Leu Ser Pro Gln Glu
595                 600                 605                 610

ATT AGT TAC TTC CAG TTC CCC GGA GAG CTC CTG ATG AGG ATG CTG AAG         374
Ile Ser Tyr Phe Gln Phe Pro Gly Glu Leu Leu Met Arg Met Leu Lys
                615                 620                 625
```

| | |
|---|---|
| ATG ATG ATC CTG CCA CTG GTG TTC TCC AGC TTG ATG TCC GGA CTT GCC<br>Met Met Ile Leu Pro Leu Val Phe Ser Ser Leu Met Ser Gly Leu Ala<br>630 635 640 | 422 |
| TCC CTG GAT GCC AAG ACC TCT AGC CGC CTG GGC GTC CTC ACC GTG GCG<br>Ser Leu Asp Ala Lys Thr Ser Ser Arg Leu Gly Val Leu Thr Val Ala<br>645 650 655 | 470 |
| TAC TAC CTG TGG ACC ACC TTC ATG GCT GTC ATC GTG GGC ATC TTC ATG<br>Tyr Tyr Leu Trp Thr Thr Phe Met Ala Val Ile Val Gly Ile Phe Met<br>660 665 670 | 518 |
| GTC TCC ATC ATC CAC CCA GGC AGC GCG GCC CAG AAG GAG ACC ACG GAG<br>Val Ser Ile Ile His Pro Gly Ser Ala Ala Gln Lys Glu Thr Thr Glu<br>675 680 685 690 | 566 |
| CAG AGT GGG AAG CCC ATC ATG AGC TCA GCC GAT GCC CTG TTG GAC CTC<br>Gln Ser Gly Lys Pro Ile Met Ser Ser Ala Asp Ala Leu Leu Asp Leu<br>695 700 705 | 614 |
| ATC CGG AAC ATG TTC CCA GCC AAC CTA GTA GAA GCC ACA TTC AAA CAG<br>Ile Arg Asn Met Phe Pro Ala Asn Leu Val Glu Ala Thr Phe Lys Gln<br>710 715 720 | 662 |
| TAC CGC ACC AAG ACC ACC CCA GTT GTC AAG TCC CCC AAG GTG GCA CCA<br>Tyr Arg Thr Lys Thr Thr Pro Val Val Lys Ser Pro Lys Val Ala Pro<br>725 730 735 | 710 |
| GAG GAG GCC CCT CCT CGG CGG ATC CTC ATC TAC GGG GTC CAG GAG GAG<br>Glu Glu Ala Pro Pro Arg Arg Ile Leu Ile Tyr Gly Val Gln Glu Glu<br>740 745 750 | 758 |
| AAT GGC TCC CAT GTG CAG AAC TTC GCC CTG GAC CTG ACC CCG CCG CCC<br>Asn Gly Ser His Val Gln Asn Phe Ala Leu Asp Leu Thr Pro Pro Pro<br>755 760 765 770 | 806 |
| GAG GTC GTT TAC AAG TCA GAG CCG GGC ACC AGC GAT GGC ATG AAT GTG<br>Glu Val Val Tyr Lys Ser Glu Pro Gly Thr Ser Asp Gly Met Asn Val<br>775 780 785 | 854 |
| CTG GGC ATC GTC TTC TTC TCT GCC ACC ATG GGC ATC ATG CTG GGC CGC<br>Leu Gly Ile Val Phe Phe Ser Ala Thr Met Gly Ile Met Leu Gly Arg<br>790 795 800 | 902 |
| ATG GGT GAC AGC GGG GGC CCC CTG GTC AGC TTC TGC CAG TGC CTC AAT<br>Met Gly Asp Ser Gly Gly Pro Leu Val Ser Phe Cys Gln Cys Leu Asn<br>805 810 815 | 950 |
| GAG TCG GTC ATG AAG ATC GTG GCG GTG GCT GTG TGG TAT TTC CCC TTC<br>Glu Ser Val Met Lys Ile Val Ala Val Ala Val Trp Tyr Phe Pro Phe<br>820 825 830 | 998 |
| GGC ATT GTG TTC CTC ATT GCG GGT AAG ATC CTG GAG ATG GAC GAC CCC<br>Gly Ile Val Phe Leu Ile Ala Gly Lys Ile Leu Glu Met Asp Asp Pro<br>835 840 845 850 | 1046 |
| AGG GCC GTC GGC AAG AAG CTG GGC TTC TAC TCA GTC ACC GTG GTG TGC<br>Arg Ala Val Gly Lys Lys Leu Gly Phe Tyr Ser Val Thr Val Val Cys<br>855 860 865 | 1094 |
| GGG CTG GTG CTC CAC GGG CTC TTT ATC CTG CCC CTG CTC TAC TTC TTC<br>Gly Leu Val Leu His Gly Leu Phe Ile Leu Pro Leu Leu Tyr Phe Phe<br>870 875 880 | 1142 |
| ATC ACC AAG AAG AAT CCC ATC GTC TTC ATC CGC GGC ATC CTG CAG GCT<br>Ile Thr Lys Lys Asn Pro Ile Val Phe Ile Arg Gly Ile Leu Gln Ala<br>885 890 895 | 1190 |
| CTC CTC ATC GCG CTG GCC ACC TCC TCC AGC TCA GCC ACA CTG CCC ATC<br>Leu Leu Ile Ala Leu Ala Thr Ser Ser Ser Ser Ala Thr Leu Pro Ile<br>900 905 910 | 1238 |
| ACC TTC AAG TGC CTG CTG GAG AAC AAC CAC ATC GAC CGG CGC ATC GCT<br>Thr Phe Lys Cys Leu Leu Glu Asn Asn His Ile Asp Arg Arg Ile Ala<br>915 920 925 930 | 1286 |
| CGC TTC GTG CTG CCC GTG GGT GCC ACC ATC AAC ATG GAC GGC ACT GCG<br>Arg Phe Val Leu Pro Val Gly Ala Thr Ile Asn Met Asp Gly Thr Ala<br>935 940 945 | 1334 |

| | | | | | | | | | | | | | | |
|---|---|---|---|---|---|---|---|---|---|---|---|---|---|---|
| CTC | TAC | GAG | GCT | GTG | GCC | GCC | ATC | TTC | ATC | GCC | CAG | GTC | AAC | AAC | TAC | 1382 |
| Leu | Tyr | Glu | Ala | Val | Ala | Ala | Ile | Phe | Ile | Ala | Gln | Val | Asn | Asn | Tyr | |
| | | 950 | | | | | 955 | | | | | 960 | | | | |

```
CTC TAC GAG GCT GTG GCC GCC ATC TTC ATC GCC CAG GTC AAC AAC TAC    1382
Leu Tyr Glu Ala Val Ala Ala Ile Phe Ile Ala Gln Val Asn Asn Tyr
        950             955             960

GAG CTG GAC TTT GGC CAG CTC ATC ACC ATC AGT ATC ACA GGC ACT GCA    1430
Glu Leu Asp Phe Gly Gln Leu Ile Thr Ile Ser Ile Thr Gly Thr Ala
        965             970             975

GCC AGC ATT GGG GCA GCT GGC ATC CCC CAG GCC GGC CTC GTC ACC ATG    1478
Ala Ser Ile Gly Ala Ala Gly Ile Pro Gln Ala Gly Leu Val Thr Met
        980             985             990

GTC ATC GTG CTC ACC TCC GTG GGA CTG CCC ACC GAT GAC ATC ACC CTC    1526
Val Ile Val Leu Thr Ser Val Gly Leu Pro Thr Asp Asp Ile Thr Leu
995             1000            1005            1010

ATC ATT GGC GTT GAC TGG GCT CTG GAC CGT TTC CGC ACC ATG ATT AAC    1574
Ile Ile Gly Val Asp Trp Ala Leu Asp Arg Phe Arg Thr Met Ile Asn
                1015            1020            1025

GTG CTG GGT GAT GCG CTG GCA GCG GGG ATC ATG GCC CAT ATA TGT CGG    1622
Val Leu Gly Asp Ala Leu Ala Ala Gly Ile Met Ala His Ile Cys Arg
                1030            1035            1040

AAG GAT TTT GCC CGG GAC ACA GGC ACC GAG AAA CTG CTG CCC TGC GAG    1670
Lys Asp Phe Ala Arg Asp Thr Gly Thr Glu Lys Leu Leu Pro Cys Glu
                1045            1050            1055

ACC AAG CCA GTG AGC CTC CAG GAG ATC GTG GCA GCC CAG CAG AAT GGC    1718
Thr Lys Pro Val Ser Leu Gln Glu Ile Val Ala Ala Gln Gln Asn Gly
        1060            1065            1070

TGT GTG AAG AGT GTA GCC GAG GCC TCC GAG CTC ACC CTG GGC CCC ACC    1766
Cys Val Lys Ser Val Ala Glu Ala Ser Glu Leu Thr Leu Gly Pro Thr
1075            1080            1085            1090

TGC CCC CAC CAC GTC CCC GTT CAA GTG GAG CGG GAT GAG GAG CTG CCC    1814
Cys Pro His His Val Pro Val Gln Val Glu Arg Asp Glu Glu Leu Pro
                1095            1100            1105

GCT GCG AGT CTG AAC CAC TGC ACC ATC CAG ATC AGC GAG CTG GAG ACC    1862
Ala Ala Ser Leu Asn His Cys Thr Ile Gln Ile Ser Glu Leu Glu Thr
                1110            1115            1120

AAT GTC TGAGCCTGCG GAGCTGCAGG GGCAGGCGAG GCCTCCAGGG GCAGGGTCCT     1918
Asn Val

GAGGCAGGAA CTCGACTCTC CAACCCTCCT GAGCAGCCGG TAGGGGGCAG GATCACACAT  1978

TCTTCTCACC CTTGAGAGGA TGGAATTAAC CCCGCTTGGA CGGAAAATGT TTCTCAAGAG  2038

AAGGGAAAGG GTGCATGGGG GAGCCCATCC AGGGAGTGAT GGGCCCGGAT TGGCTGAAGG  2098

CCCCTTGTGA AAGTTTCCCC CGTTGTGAAC CCCGGTGAAG GGGGGAAGGC AGGGGGTTTT  2158

CCGGCCCCCC TTTTCTTGGA TGATAGGATT TGGACC                           2194
```

(2) INFORMATION FOR SEQ ID NO:10:

(i) SEQUENCE CHARACTERISTICS:
        (A) LENGTH: 560 amino acids
        (B) TYPE: amino acid
        (D) TOPOLOGY: linear (ii) MOLECULE TYPE: protein (xi) SEQUENCE DESCRIPTION: SEQ ID NO:10:

```
Met Val Pro His Thr Ile Leu Ala Arg Gly Arg Asp Val Cys Arg Arg
1               5                   10                  15

Asn Gly Leu Leu Ile Leu Ser Val Leu Ser Val Ile Val Gly Cys Leu
            20                  25                  30

Leu Gly Phe Phe Leu Arg Thr Arg Arg Leu Ser Pro Gln Glu Ile Ser
        35                  40                  45

Tyr Phe Gln Phe Pro Gly Glu Leu Leu Met Arg Met Leu Lys Met Met
    50                  55                  60
```

```
Ile Leu Pro Leu Val Phe Ser Ser Leu Met Ser Gly Leu Ala Ser Leu
 65                  70                  75                  80

Asp Ala Lys Thr Ser Ser Arg Leu Gly Val Leu Thr Val Ala Tyr Tyr
                 85                  90                  95

Leu Trp Thr Thr Phe Met Ala Val Ile Val Gly Ile Phe Met Val Ser
            100                 105                 110

Ile Ile His Pro Gly Ser Ala Ala Gln Lys Glu Thr Thr Glu Gln Ser
        115                 120                 125

Gly Lys Pro Ile Met Ser Ser Ala Asp Ala Leu Leu Asp Leu Ile Arg
    130                 135                 140

Asn Met Phe Pro Ala Asn Leu Val Glu Ala Thr Phe Lys Gln Tyr Arg
145                 150                 155                 160

Thr Lys Thr Thr Pro Val Val Lys Ser Pro Lys Val Ala Pro Glu Glu
                165                 170                 175

Ala Pro Pro Arg Arg Ile Leu Ile Tyr Gly Val Gln Glu Glu Asn Gly
            180                 185                 190

Ser His Val Gln Asn Phe Ala Leu Asp Leu Thr Pro Pro Glu Val
        195                 200                 205

Val Tyr Lys Ser Glu Pro Gly Thr Ser Asp Gly Met Asn Val Leu Gly
    210                 215                 220

Ile Val Phe Phe Ser Ala Thr Met Gly Ile Met Leu Gly Arg Met Gly
225                 230                 235                 240

Asp Ser Gly Gly Pro Leu Val Ser Phe Cys Gln Cys Leu Asn Glu Ser
                245                 250                 255

Val Met Lys Ile Val Ala Val Ala Val Trp Tyr Phe Pro Phe Gly Ile
            260                 265                 270

Val Phe Leu Ile Ala Gly Lys Ile Leu Glu Met Asp Asp Pro Arg Ala
        275                 280                 285

Val Gly Lys Lys Leu Gly Phe Tyr Ser Val Thr Val Val Cys Gly Leu
    290                 295                 300

Val Leu His Gly Leu Phe Ile Leu Pro Leu Leu Tyr Phe Phe Ile Thr
305                 310                 315                 320

Lys Lys Asn Pro Ile Val Phe Ile Arg Gly Ile Leu Gln Ala Leu Leu
                325                 330                 335

Ile Ala Leu Ala Thr Ser Ser Ser Ala Thr Leu Pro Ile Thr Phe
        340                 345                 350

Lys Cys Leu Leu Glu Asn Asn His Ile Asp Arg Arg Ile Ala Arg Phe
    355                 360                 365

Val Leu Pro Val Gly Ala Thr Ile Asn Met Asp Gly Thr Ala Leu Tyr
370                 375                 380

Glu Ala Val Ala Ala Ile Phe Ile Ala Gln Val Asn Asn Tyr Glu Leu
385                 390                 395                 400

Asp Phe Gly Gln Leu Ile Thr Ile Ser Ile Thr Gly Thr Ala Ala Ser
                405                 410                 415

Ile Gly Ala Ala Gly Ile Pro Gln Ala Gly Leu Val Thr Met Val Ile
            420                 425                 430

Val Leu Thr Ser Val Gly Leu Pro Thr Asp Asp Ile Thr Leu Ile Ile
        435                 440                 445

Gly Val Asp Trp Ala Leu Asp Arg Phe Arg Thr Met Ile Asn Val Leu
    450                 455                 460

Gly Asp Ala Leu Ala Ala Gly Ile Met Ala His Ile Cys Arg Lys Asp
465                 470                 475                 480

Phe Ala Arg Asp Thr Gly Thr Glu Lys Leu Leu Pro Cys Glu Thr Lys
```

485                 490                 495
Pro Val Ser Leu Gln Glu Ile Val Ala Ala Gln Gln Asn Gly Cys Val
            500                 505                 510

Lys Ser Val Ala Glu Ala Ser Glu Leu Thr Leu Gly Pro Thr Cys Pro
        515                 520                 525

His His Val Pro Val Gln Val Glu Arg Asp Glu Glu Leu Pro Ala Ala
    530                 535                 540

Ser Leu Asn His Cys Thr Ile Gln Ile Ser Glu Leu Glu Thr Asn Val
545                 550                 555                 560

(2) INFORMATION FOR SEQ ID NO:11:

(i) SEQUENCE CHARACTERISTICS:
        (A) LENGTH: 1912 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 83..1774

(xi) SEQUENCE DESCRIPTION: SEQ ID NO:11:

GAATTCGCGG CCGCGTCGAC GGAACCCCGG CGCCCTGTCT CAATGGGCAG CGGGCCCACC         60

CCCAAGGACC ACTGAGGACG CC ATG GCG GTG ACT GTG GAC GCG ATG CTG GCT        112
                        Met Ala Val Thr Val Asp Ala Met Leu Ala
                                        565                 570

CGC GCC AAG GAT GTC TGT AAG AGG AAC GGC CTG CTC ATC TTG TCC GTC        160
Arg Ala Lys Asp Val Cys Lys Arg Asn Gly Leu Leu Ile Leu Ser Val
                575                 580                 585

TTG TCC GTC ATC ATA GGG TGT CTG CTG GGG TTC TTC CTG AGG ACT CGT        208
Leu Ser Val Ile Ile Gly Cys Leu Leu Gly Phe Phe Leu Arg Thr Arg
            590                 595                 600

CGC CTG TGT GAG CAG GAA ATA AGC TAC TTC CAG TTT CCT GGA GAG CTG        256
Arg Leu Cys Glu Gln Glu Ile Ser Tyr Phe Gln Phe Pro Gly Glu Leu
        605                 610                 615

CTG ATG AGG ATG CTG AAG ATG CTG ATT CTC CCG CTG GTC GTC TCA AGC        304
Leu Met Arg Met Leu Lys Met Leu Ile Leu Pro Leu Val Val Ser Ser
    620                 625                 630

TTA ATG TCA GGG TTG GCG GCC TTG GAT GCC AAG ACT TCC AGC CGG CTC        352
Leu Met Ser Gly Leu Ala Ala Leu Asp Ala Lys Thr Ser Ser Arg Leu
635                 640                 645                 650

GGC ATC ATA ACC ATC GCT TAC TAC CTG TGG ACG ACC TTT GTG GCA GTC        400
Gly Ile Ile Thr Ile Ala Tyr Tyr Leu Trp Thr Thr Phe Val Ala Val
                655                 660                 665

ATA GTG GGG ATT GTC ATG GTC TCC ATA ATT CAC CCT GGA GGA GCG GCC        448
Ile Val Gly Ile Val Met Val Ser Ile Ile His Pro Gly Gly Ala Ala
            670                 675                 680

CAG AAG GAG AAC ACC GAC CAG AGT GGG AAG CCC ATC ATG AGC TCC GCC        496
Gln Lys Glu Asn Thr Asp Gln Ser Gly Lys Pro Ile Met Ser Ser Ala
        685                 690                 695

GAT GCC TTA CTA GAC CTC ATT AGG AAT ATG TTT CCA GCT AAC CTT GTT        544
Asp Ala Leu Leu Asp Leu Ile Arg Asn Met Phe Pro Ala Asn Leu Val
    700                 705                 710

GAA GCT ACA TTT AAA CAG TAC CGT ACC AAG AAC ACT CCC ATT GTC AAA        592
Glu Ala Thr Phe Lys Gln Tyr Arg Thr Lys Asn Thr Pro Ile Val Lys
715                 720                 725                 730

ACC GGT AAG GTG CCT CCT TCT GAA AGC ATC ACC CAT CGG ATC CTA GTC        640
Thr Gly Lys Val Pro Pro Ser Glu Ser Ile Thr His Arg Ile Leu Val
                735                 740                 745

```
TAC GGG ATC CAG GAT GAG AAT GGA TCA AAC ATC CAG AAC TTT GCA CTG      688
Tyr Gly Ile Gln Asp Glu Asn Gly Ser Asn Ile Gln Asn Phe Ala Leu
            750                 755                 760

GAC ATC ACG CCA CCG CCA GAG GTG ATC TAC AAA TCT GAG CCT GGC ACC      736
Asp Ile Thr Pro Pro Pro Glu Val Ile Tyr Lys Ser Glu Pro Gly Thr
            765                 770                 775

AGC GAA GGC ATG AAT GTG CTG GGC ATT GTG ATC TTC TCT GCA ACG ATG      784
Ser Glu Gly Met Asn Val Leu Gly Ile Val Ile Phe Ser Ala Thr Met
780                 785                 790

GGA ATA ATG CTG GGG AGA ATG GGC ACC AGC GGG GTC CCG GTG GTC AGC      832
Gly Ile Met Leu Gly Arg Met Gly Thr Ser Gly Val Pro Val Val Ser
795                 800                 805                 810

TTC TGC CAG TGT CTG AAT GAA TCT GTG ATG AAG ATA GTG GCT GTC TCC      880
Phe Cys Gln Cys Leu Asn Glu Ser Val Met Lys Ile Val Ala Val Ser
                815                 820                 825

GTG TGG TAT TTC CCA TTT GGC ATC GTA TTC CTC ATT GCA GGA AAG ATA      928
Val Trp Tyr Phe Pro Phe Gly Ile Val Phe Leu Ile Ala Gly Lys Ile
            830                 835                 840

TTG GAG ATG GAT GAC CCA ACA GCC TTC GGG AAG AAA CTG GGC TTT TAC      976
Leu Glu Met Asp Asp Pro Thr Ala Phe Gly Lys Lys Leu Gly Phe Tyr
            845                 850                 855

GCC ATC ACT GTG GTT TGT GGC TTG GTC GTG CAT GGA CTT TTC ATT CTG     1024
Ala Ile Thr Val Val Cys Gly Leu Val Val His Gly Leu Phe Ile Leu
            860                 865                 870

CCA ATG ATG TAT CTC TTC ATC ACC AAG AAA AAC CCC ATT GTC TTC ATC     1072
Pro Met Met Tyr Leu Phe Ile Thr Lys Lys Asn Pro Ile Val Phe Ile
875                 880                 885                 890

CGG GGG GTT CTT CAA GCC TTG CTC ATA GCT CTG GCC ACG TCA TCC AGC     1120
Arg Gly Val Leu Gln Ala Leu Leu Ile Ala Leu Ala Thr Ser Ser Ser
                895                 900                 905

TCG GCC ACA TTG CCT ATA ACC TTC AAG TGT TTG CTG GAG AAT AAT CAC     1168
Ser Ala Thr Leu Pro Ile Thr Phe Lys Cys Leu Leu Glu Asn Asn His
            910                 915                 920

ATT GAC AGA AGG ATT GCC AGG TTT GTG CTG CCT GTG GGA GCC ACC ATT     1216
Ile Asp Arg Arg Ile Ala Arg Phe Val Leu Pro Val Gly Ala Thr Ile
            925                 930                 935

AAC ATG GAT GGA ACC GCT CTT TAT GAA GCC GTG GCG GCC ATC TTT ATT     1264
Asn Met Asp Gly Thr Ala Leu Tyr Glu Ala Val Ala Ala Ile Phe Ile
940                 945                 950

GCT CAA GTG AAC AAC TAT GAA CTA GAC TTT GGG CAG ATT ATT ACC ATA     1312
Ala Gln Val Asn Asn Tyr Glu Leu Asp Phe Gly Gln Ile Ile Thr Ile
955                 960                 965                 970

AGC ATC ACA GCA ACA GCC GCC AGT ATC GGG GCA GCG GGC ATT CCA CAG     1360
Ser Ile Thr Ala Thr Ala Ala Ser Ile Gly Ala Ala Gly Ile Pro Gln
                975                 980                 985

GCT GGC CTT GTG ACA ATG GTC ATC GTG CTC ACA TCA GTC GGG CTA CCT     1408
Ala Gly Leu Val Thr Met Val Ile Val Leu Thr Ser Val Gly Leu Pro
            990                 995                 1000

ACC GAT GAC ATC ACT CTC ATC ATC GCT GTG GAC TGG GCA CTA GAT CGA     1456
Thr Asp Asp Ile Thr Leu Ile Ile Ala Val Asp Trp Ala Leu Asp Arg
            1005                1010                1015

TTT AGA ACA ATG ATC AAC GTC TTG GGA GAT GCC TTG GCT GCT GGG ATC     1504
Phe Arg Thr Met Ile Asn Val Leu Gly Asp Ala Leu Ala Ala Gly Ile
            1020                1025                1030

ATG GCT CAC ATC TGC AGA AAG GAT TTT GAA AAC CAG AAC GAT GAG GTT     1552
Met Ala His Ile Cys Arg Lys Asp Phe Glu Asn Gln Asn Asp Glu Val
1035                1040                1045                1050

CCA CTG ATC TGT GAA ACG AAA AAT TTT AGC ATC CAC CAA ATC ATG GCG     1600
Pro Leu Ile Cys Glu Thr Lys Asn Phe Ser Ile His Gln Ile Met Ala
                1055                1060                1065
```

```
TAC CAG AGA AAC GGC TGC GTG AAA AAT ATG AAC GCT TAT CAC GGG CAG      1648
Tyr Gln Arg Asn Gly Cys Val Lys Asn Met Asn Ala Tyr His Gly Gln
            1070                1075                1080

GAG ACA GTG AAA GAC TGT CAT TAC ATA GAC ATG GAG CCG GAA GGT GCC      1696
Glu Thr Val Lys Asp Cys His Tyr Ile Asp Met Glu Pro Glu Gly Ala
        1085                1090                1095

CCG GAG GAG AAC CAC ATT GAG GTA TCC AAC GAC AAG GAC CAC TGC ACC      1744
Pro Glu Glu Asn His Ile Glu Val Ser Asn Asp Lys Asp His Cys Thr
    1100                1105                1110

ATT GAG ATC AAT GAA GTT GAA ACA AAC GTG TAGCTGATTG CCATGCAAAC        1794
Ile Glu Ile Asn Glu Val Glu Thr Asn Val
1115                1120

CTCATCTGCT ACTGGAGAGG GGACAATGGT GGCAGAACCA GCAGCTCTGA GTAAATAAGG    1854

CCCTAAAGAT GACAGACTCG ACAATTGTGC ATTTATCTGA GGCACAAATT CATTAAGG      1912

(2) INFORMATION FOR SEQ ID NO:12:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:12:

Met Ala Val Thr Val Asp Ala Met Leu Ala Arg Ala Lys Asp Val Cys
1               5                   10                  15

Lys Arg Asn Gly Leu Leu Ile Leu Ser Val Leu Ser Val Ile Ile Gly
            20                  25                  30

Cys Leu Leu Gly Phe Phe Leu Arg Thr Arg Arg Leu Cys Glu Gln Glu
        35                  40                  45

Ile Ser Tyr Phe Gln Phe Pro Gly Glu Leu Leu Met Arg Met Leu Lys
    50                  55                  60

Met Leu Ile Leu Pro Leu Val Val Ser Ser Leu Met Ser Gly Leu Ala
65                  70                  75                  80

Ala Leu Asp Ala Lys Thr Ser Ser Arg Leu Gly Ile Ile Thr Ile Ala
                85                  90                  95

Tyr Tyr Leu Trp Thr Thr Phe Val Ala Val Ile Val Gly Ile Val Met
            100                 105                 110

Val Ser Ile Ile His Pro Gly Gly Ala Ala Gln Lys Glu Asn Thr Asp
        115                 120                 125

Gln Ser Gly Lys Pro Ile Met Ser Ser Ala Asp Ala Leu Leu Asp Leu
    130                 135                 140

Ile Arg Asn Met Phe Pro Ala Asn Leu Val Glu Ala Thr Phe Lys Gln
145                 150                 155                 160

Tyr Arg Thr Lys Asn Thr Pro Ile Val Lys Thr Gly Lys Val Pro Pro
                165                 170                 175

Ser Glu Ser Ile Thr His Arg Ile Leu Val Tyr Gly Ile Gln Asp Glu
            180                 185                 190

Asn Gly Ser Asn Ile Gln Asn Phe Ala Leu Asp Ile Thr Pro Pro Pro
        195                 200                 205

Glu Val Ile Tyr Lys Ser Glu Pro Gly Thr Ser Glu Gly Met Asn Val
    210                 215                 220

Leu Gly Ile Val Ile Phe Ser Ala Thr Met Gly Ile Met Leu Gly Arg
225                 230                 235                 240

Met Gly Thr Ser Gly Val Pro Val Val Ser Phe Cys Gln Cys Leu Asn
                245                 250                 255
```

```
Glu Ser Val Met Lys Ile Val Ala Val Ser Val Trp Tyr Phe Pro Phe
            260                 265                 270
Gly Ile Val Phe Leu Ile Ala Gly Lys Ile Leu Glu Met Asp Asp Pro
            275                 280                 285
Thr Ala Phe Gly Lys Lys Leu Gly Phe Tyr Ala Ile Thr Val Val Cys
            290                 295                 300
Gly Leu Val Val His Gly Leu Phe Ile Leu Pro Met Met Tyr Leu Phe
305                 310                 315                 320
Ile Thr Lys Lys Asn Pro Ile Val Phe Ile Arg Gly Val Leu Gln Ala
            325                 330                 335
Leu Leu Ile Ala Leu Ala Thr Ser Ser Ser Ala Thr Leu Pro Ile
            340                 345                 350
Thr Phe Lys Cys Leu Leu Glu Asn Asn His Ile Asp Arg Arg Ile Ala
            355                 360                 365
Arg Phe Val Leu Pro Val Gly Ala Thr Ile Asn Met Asp Gly Thr Ala
            370                 375                 380
Leu Tyr Glu Ala Val Ala Ala Ile Phe Ile Ala Gln Val Asn Asn Tyr
385                 390                 395                 400
Glu Leu Asp Phe Gly Gln Ile Ile Thr Ile Ser Ile Thr Ala Thr Ala
            405                 410                 415
Ala Ser Ile Gly Ala Ala Gly Ile Pro Gln Ala Gly Leu Val Thr Met
            420                 425                 430
Val Ile Val Leu Thr Ser Val Gly Leu Pro Thr Asp Asp Ile Thr Leu
            435                 440                 445
Ile Ile Ala Val Asp Trp Ala Leu Asp Arg Phe Arg Thr Met Ile Asn
450                 455                 460
Val Leu Gly Asp Ala Leu Ala Ala Gly Ile Met Ala His Ile Cys Arg
465                 470                 475                 480
Lys Asp Phe Glu Asn Gln Asn Asp Glu Val Pro Leu Ile Cys Glu Thr
            485                 490                 495
Lys Asn Phe Ser Ile His Gln Ile Met Ala Tyr Gln Arg Asn Gly Cys
            500                 505                 510
Val Lys Asn Met Asn Ala Tyr His Gly Gln Glu Thr Val Lys Asp Cys
            515                 520                 525
His Tyr Ile Asp Met Glu Pro Glu Gly Ala Pro Glu Glu Asn His Ile
530                 535                 540
Glu Val Ser Asn Asp Lys Asp His Cys Thr Ile Glu Ile Asn Glu Val
545                 550                 555                 560
Glu Thr Asn Val (2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CGCGGGTACC CTACCATGGT GCCGCAT                                               27

(2) INFORMATION FOR SEQ ID NO:14:

(i) SEQUENCE CHARACTERISTICS:
        (A) LENGTH: 28 base pairs
```

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CGCGTCTAGA GGCTCAGACA TTGGTCTC                                          28
```